US010194644B2

(12) United States Patent
Lauth et al.

(10) Patent No.: US 10,194,644 B2
(45) Date of Patent: *Feb. 5, 2019

(54) MATERNALLY INDUCED STERILITY IN ANIMALS

(71) Applicant: AquaBounty Technologies, Inc., Maynard, MA (US)

(72) Inventors: Xavier Lauth, San Diego, CA (US); John T. Buchanan, San Diego, CA (US)

(73) Assignee: AquaBounty Technologies, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/928,463

(22) Filed: Oct. 30, 2015

(65) Prior Publication Data
US 2016/0050894 A1 Feb. 25, 2016

Related U.S. Application Data

(63) Continuation of application No. 13/511,317, filed as application No. PCT/US2010/057863 on Nov. 23, 2010, now Pat. No. 9,198,404.

(60) Provisional application No. 61/263,468, filed on Nov. 23, 2009.

(51) Int. Cl.
A01K 67/027 (2006.01)
C12N 15/85 (2006.01)
C07K 14/47 (2006.01)

(52) U.S. Cl.
CPC ...... A01K 67/0275 (2013.01); C07K 14/4747 (2013.01); C12N 15/8509 (2013.01); A01K 2207/05 (2013.01); A01K 2217/052 (2013.01); A01K 2217/206 (2013.01); A01K 2227/40 (2013.01); A01K 2267/03 (2013.01); C12N 2800/80 (2013.01); Y02A 90/40 (2018.01)

(58) Field of Classification Search
CPC .......... A01K 2207/05; A01K 2217/052; A01K 2227/40; A01K 67/0275; C12N 2517/02
See application file for complete search history.

(56) References Cited

U.S. PATENT DOCUMENTS

2005/0071891 A1  3/2005  Thresher et al.
2010/0212039 A1*  8/2010  Wu ................... A01K 67/0275
                                                             800/20

FOREIGN PATENT DOCUMENTS

JP       2008521441       6/2008

OTHER PUBLICATIONS

Hashimoto et al Developmental Biology, 2004, 268, 152-161.*
Nofima (online); Aug. 5, 2009 Generation of gonadless farmed cod by specific ablation of primordial germ cells.*
Blaser et all J. Cell Sci.; 2005, 118(Pt. 17):4027-4038.*
Slanchev et al Proc. Natl. Acad. Sci. USA; 2005, 102(11 ):4074-4079.*
Rucker et al Mol Endocrinol.; 2000, 14(7):1038-1052.*
Uzbekova et al Journal of Molecular Endocrinology (2000) 25, 337-350.*
The International Search Report and Written Opinion from PCT/US2010/057863, dated Feb. 28, 2011.
Blaser et al.; "Transition from non-motile behaviour to directed migration during early PGC development in zebrafish"; J. Cell Sci.; 118(Pt. 17):4027-4038 (2005).
Rucker et al.; "Bcl-x and Bax regulate mouse primordial germ cell survival and apoptosis during embryogenesis"; Mol Endocrinol.; 14(7):1038-1052 (2000).
Slanchev et al.; "Development without germ cells: the role of the germ line in zebrafish sex differentiation"; Proc. Natl. Acad. Sci. USA; 102(11):4074-4079 (2005).
"Generation of gonadless farmed cod by specific ablation of primordial germ cells"; Nofima (online); Aug. 5, 2009. With Index. Retrieved from the internet on Feb. 16, 2011 at URL:<http://www.nofima.no/marin/en/prosjekt/4488572443978722692>.
Wong et al.; "Transgenic approaches for reproductive containment of genetically engineered fish"; Aquaculture; 275:1-12 (2008).
Lin et al.; "Specific Gene Expression of Nitroreductase in Zebrafish Primordial Germ Cells for the Inhibition of Gonadal Development" (2009) online Retrieved from the Internet on Jan. 26, 2011 at <URL:http:I/ntur.lib.ntu.edu.tw/handle/246246/181722>; abstract only.
"Genetic and reproduction technologies for enhanced production of Murray cod"; Department of Primary Industries, Melbourne, Victoria Australia, Technical Note 17, (2007) Retrieved Feb. 16, 2011 from the internet URL:<http://www.dpi.vic.gov.au/dpi/nrenfaq.nsf/LinkView/008 1 A871 006912F9CA25750800189071858CE8A03 2C48CE1CA2573DA0014A8EBI$file/Genetic%20and%20reproduction%20technologies%20for%20enhancedo/o20production%20of%20Murray%20cod.pdf>.
Hashimoto et al., "Localized maternal factors are required for zebrafish germ cell formation", Developmental Biology 268:152-161 (2004).
Ewen-Campen et al., "Germ Cell Specification Requires Zygotic Mechanisms Rathr Than Germ Plasm in a Basally Branching Insect", Current Biology, 23:835-842 (2013).

(Continued)

Primary Examiner — Anoop K Singh
(74) Attorney, Agent, or Firm — Kilpatrick Townsend & Stockton LLP

(57) ABSTRACT

The present invention provides Maternal Sterility Constructs (MSC) and methods of producing sterile progeny lacking germ cells. Female fish carrying the MSC transgene will give rise to a sterile generation, as the MSC specifically eliminates Progenitor Germ Cells (PGCs) of her progeny. These females are called lineage ending females. Male fish carrying the MSC transgene, however, give rise to fertile progeny (assuming the male is not derived from an MSC-transgenic female). Thus, MSC transgenic males can be used to propagate the transgenic line. The invention can be advantageously applied to provide effective population control and improve culture performance of farmed species, such as fish.

3 Claims, 9 Drawing Sheets
Specification includes a Sequence Listing.

(56) References Cited

OTHER PUBLICATIONS

Extavour et al., "The fate of isolated blastomeres with respect to germ cell formation in the amphipod crustacean *Parhyale hawaiensis*" *Developmental Biology*, 277:387-402 (2005).
Bartley et al., "The use of inter-specific hubrids in aquaculture and fisheries", *Reviews in Fish Biology and Fisheries*, 10:325-337 (2001).
Nofima et al., Generation of gonadless farmed cod by specific ablation of primordial germ cells (Aug. 5, 2009).
Slanchev et al., "Development without germ cells: the role of the germ line in zebrafish sex differentiation", *Proc. Natl. Acad. Sci*, 102(11):4074-4079 (2005).
Uzekova et al., "Transgenic rainbow trout expressed sGnRH-antisense RNA under the control of sGnRH promoter of Atlantic salmon" *Journal of Molecular Endocrinology*, 25:337-350 (2000).
Wong et al.,"A controllable on-off strategy for the reproductive containment of fish", *Aquaculture*, 275:1-12 (2008).
Extavour et al., "Mechanisms of germ cell specification across the metazoans: epigenesis and preformation", Development, val. 130, No. 24, Dec. 15, 2003, pp. 5869-5884.
Thresher et al., "Development of repressible sterility to prevent the establishment of feral populations of exotic and genetically modified animals", Aquaculture, Elsevier, Amsterdam, NL, vol. 290, No. 1-2, 2009, pp. 104-109.
EP10832372.6 , "Extended European Search Report", 8 pages.

\* cited by examiner

1. Introduce Maternal Sterility Construct (MSC) into progenitor cells 

to create MSC transgenic founder animal
capable of germ line transmission of MSC transgene.

2. Cross founder animal with MSC negative animal

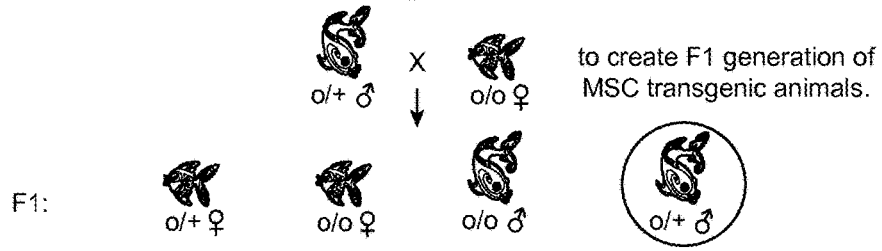

to create F1 generation of MSC transgenic animals.

3. Cross hemizygous MSC transgenic ♂ with MSC negative ♀

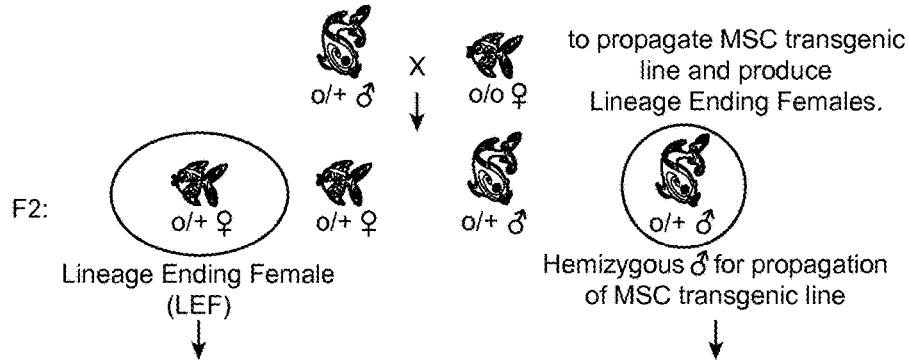

to propagate MSC transgenic line and produce Lineage Ending Females.

Lineage Ending Female (LEF)

Hemizygous ♂ for propagation of MSC transgenic line

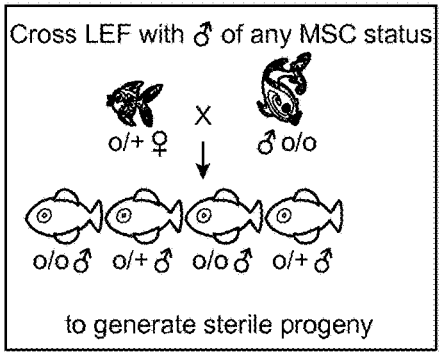

Cross LEF with ♂ of any MSC status to generate sterile progeny

AND OR

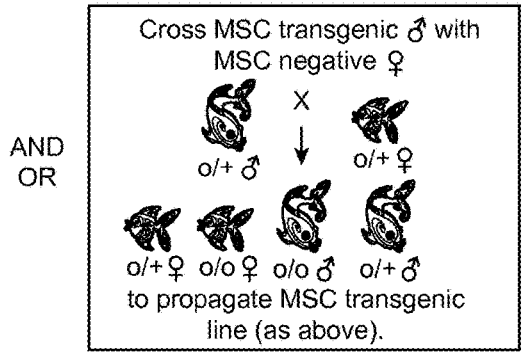

Cross MSC transgenic ♂ with MSC negative ♀ to propagate MSC transgenic line (as above).

FIG. 1

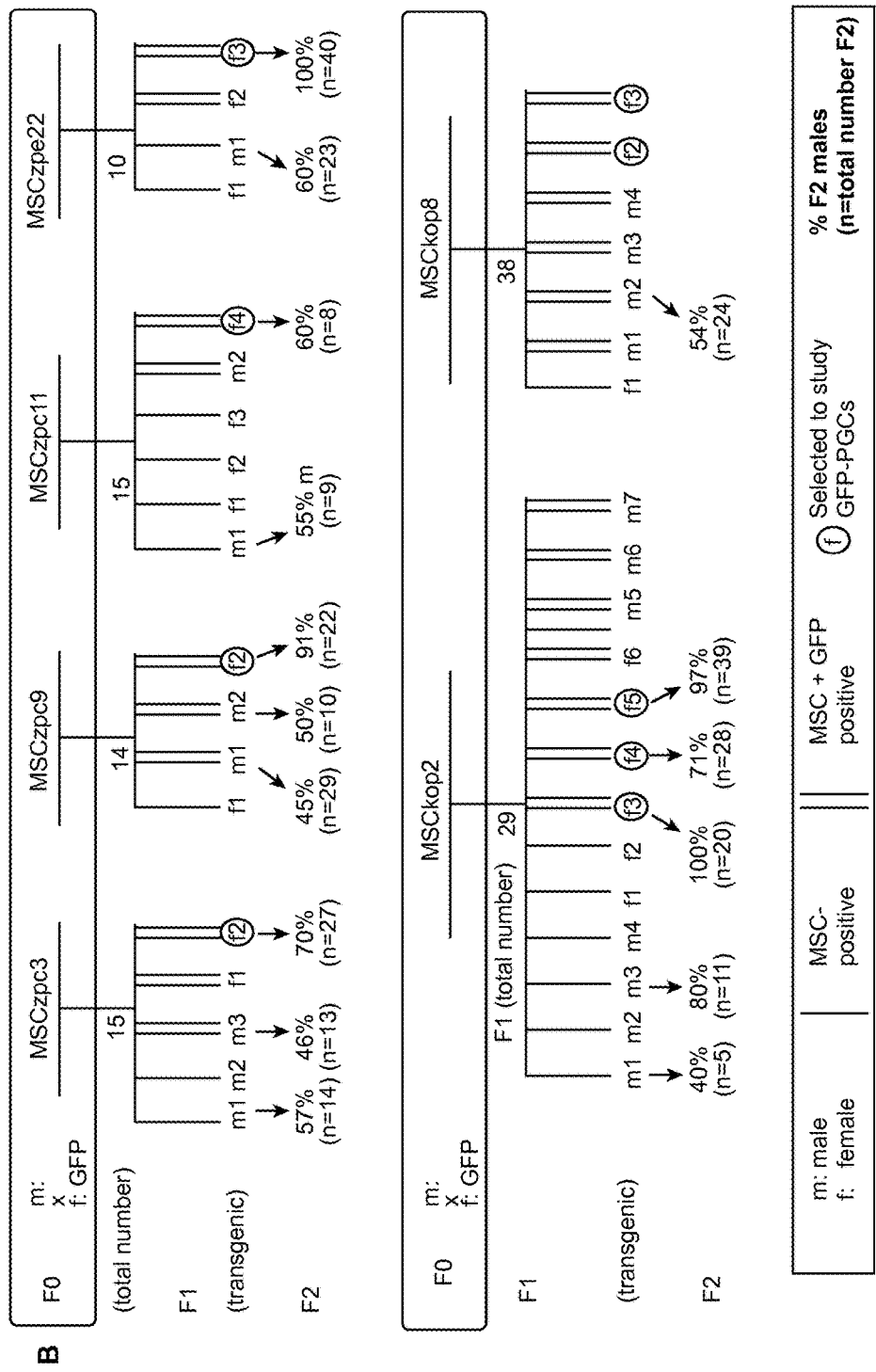
FIG. 5 (Cont. 1)

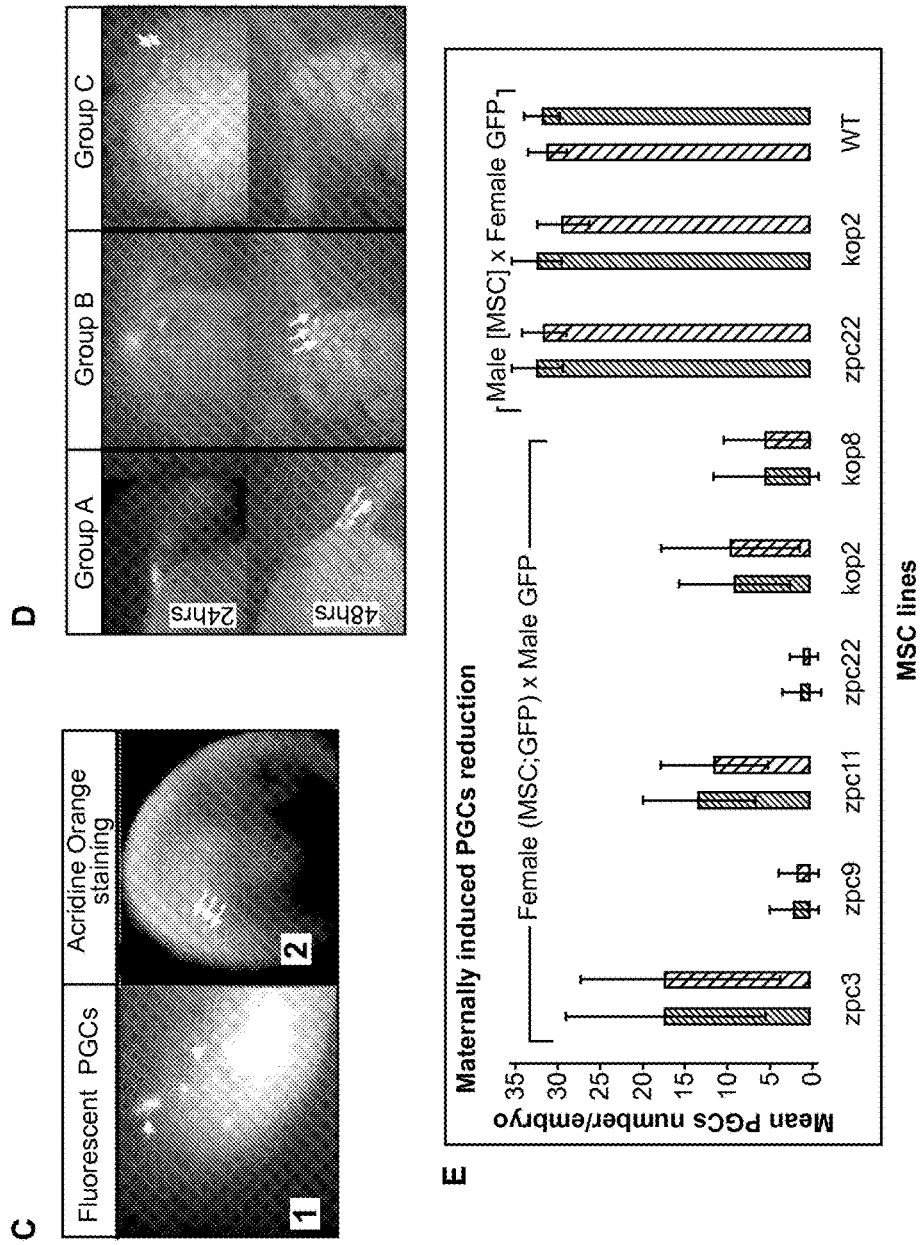
FIG. 5 (Cont.2)

SEQUENCE LISTING

<160> NUMBER OF SEQ ID NOS: 20

<210> SEQ ID NO 1
<211> LENGTH: 27
<212> TYPE: DNA
<213> ORGANISM: Artificial Sequence
<220> FEATURE:
<223> OTHER INFORMATION: synthetic oligonucleotide PCR amplification
      sense primer for nanos 1 3' UTR (nos1)

<400> SEQUENCE: 1
gcgaagcttg atgctccggg agatttg                                          27

<210> SEQ ID NO 2
<211> LENGTH: 31
<212> TYPE: DNA
<213> ORGANISM: Artificial Sequence
<220> FEATURE:
<223> OTHER INFORMATION: synthetic oligonucleotide PCR amplification
      antisense primer for nanos 1 3' UTR (nos1)

<400> SEQUENCE: 2
cccaagctta gagaaaatgt ttatattttc c                                     31

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide PCR amplification
      primer flanking Salmo salar bax (ssbax) coding sequence

<400> SEQUENCE: 3
atggcagact cccgagaaag aag                                              23

<210> SEQ ID NO 4
<211> LENGTH: 22
<212> TYPE: DNA
<213> ORGANISM: Artificial Sequence
<220> FEATURE:
<223> OTHER INFORMATION: synthetic oligonucleotide PCR amplification
      primer flanking Salmo salar bax (ssbax) coding sequence

<400> SEQUENCE: 4
tcagcgtgtt ttcctccagt aa                                               22

<210> SEQ ID NO 5
<211> LENGTH: 22
<212> TYPE: DNA
<213> ORGANISM: Artificial Sequence
<220> FEATURE:
<223> OTHER INFORMATION: synthetic quantitative real time PCR (qRT-PCR)
      amplification primer bax fwd for maternal sterility construct
      (MSC) specific junction between bax and dnd

<400> SEQUENCE: 5

```
gttattttgg cacccccacc tg                                              22
```

```
<210> SEQ ID NO 6
<211> LENGTH: 24
<212> TYPE: DNA
<213> ORGANISM: Artificial Sequence
<220> FEATURE:
<223> OTHER INFORMATION: synthetic quantitative real time PCR (qRT-PCR)
      amplification primer dead end rev for maternal sterility construct
      (MSC) specific junction between bax and dnd

<400> SEQUENCE: 6
caatcacatt cgatcaagcc ataa                                            24

<210> SEQ ID NO 7
<211> LENGTH: 19
<212> TYPE: DNA
<213> ORGANISM: Artificial Sequence
<220> FEATURE:
<223> OTHER INFORMATION: synthetic green fluorescent protein (GFP)
      specific primer Fwd

<400> SEQUENCE: 7
tacggcgtgc agtgccttc                                                  19

<210> SEQ ID NO 8
<211> LENGTH: 17
<212> TYPE: DNA
<213> ORGANISM: Artificial Sequence
<220> FEATURE:
<223> OTHER INFORMATION: synthetic green fluorescent protein (GFP)
      specific primer Rev

<400> SEQUENCE: 8
tgcgctcctg gagtagc                                                    17

<210> SEQ ID NO 9
<211> LENGTH: 24
<212> TYPE: DNA
<213> ORGANISM: Artificial Sequence
<220> FEATURE:
<223> OTHER INFORMATION: synthetic real time PCR (RT-PCR) primer vasa
      fwd

<400> SEQUENCE: 9
tggactatat tttccttgct gttg                                            24

<210> SEQ ID NO 10
<211> LENGTH: 19
<212> TYPE: DNA
<213> ORGANISM: Artificial Sequence
<220> FEATURE:
<223> OTHER INFORMATION: synthetic quantitative real time PCR (qRT-PCR)
      primer vasa fwd

<400> SEQUENCE: 10
cgtgagtggc agcaatcct                                                  19

<210> SEQ ID NO 11
<211> LENGTH: 23
<212> TYPE: DNA
<213> ORGANISM: Artificial Sequence
<220> FEATURE:
<223> OTHER INFORMATION: synthetic real time PCR (RT-PCR) primer zbvasa
      rev

<400> SEQUENCE: 11
```

```
tattcccatt cctcatcgtc tgc                                              23

<210> SEQ ID NO 12
<211> LENGTH: 21
<212> TYPE: DNA
<213> ORGANISM: Artificial Sequence
<220> FEATURE:
<223> OTHER INFORMATION: synthetic quantitative real time PCR (qRT-PCR)
      primer zbvasa rev

<400> SEQUENCE: 12
gtgtaggctt cacatatcca g                                                21

<210> SEQ ID NO 13
<211> LENGTH: 21
<212> TYPE: DNA
<213> ORGANISM: Artificial Sequence
<220> FEATURE:
<223> OTHER INFORMATION: synthetic real time PCR (RT-PCR) primer zb
      sox9a fwd

<400> SEQUENCE: 13
caccctacgc tggaggatac g                                                21

<210> SEQ ID NO 14
<211> LENGTH: 20
<212> TYPE: DNA
<213> ORGANISM: Artificial Sequence
<220> FEATURE:
<223> OTHER INFORMATION: synthetic quantitative real time PCR (qRT-PCR)
      primer zb sox9a fwd

<400> SEQUENCE: 14
cggtgaagaa cggccagagc                                                  20

<210> SEQ ID NO 15
<211> LENGTH: 21
<212> TYPE: DNA
<213> ORGANISM: Artificial Sequence
<220> FEATURE:
<223> OTHER INFORMATION: synthetic real time PCR (RT-PCR) primer zb
      sox9a rev

<400> SEQUENCE: 15
ccatcatgca ctgaacgaac a                                                21

<210> SEQ ID NO 16
<211> LENGTH: 20
<212> TYPE: DNA
<213> ORGANISM: Artificial Sequence
<220> FEATURE:
<223> OTHER INFORMATION: synthetic quantitative real time PCR (qRT-PCR)
      primer zb sox9a rev

<400> SEQUENCE: 16
ctgtagagtc agcaatgggt                                                  20

<210> SEQ ID NO 17
<211> LENGTH: 21
<212> TYPE: DNA
<213> ORGANISM: Artificial Sequence
<220> FEATURE:
<223> OTHER INFORMATION: synthetic real time PCR (RT-PCR) primer
      beta-actin fwd

<400> SEQUENCE: 17
gacatcaagg agaagctgtg c                                                21
```

```
<210> SEQ ID NO 18
<211> LENGTH: 21
<212> TYPE: DNA
<213> ORGANISM: Artificial Sequence
<220> FEATURE:
<223> OTHER INFORMATION: synthetic real time PCR (RT-PCR) primer
      beta-actin rev

<400> SEQUENCE: 18
gaggagggca aagtggtaaa c                                              21

<210> SEQ ID NO 19
<211> LENGTH: 20
<212> TYPE: DNA
<213> ORGANISM: Artificial Sequence
<220> FEATURE:
<223> OTHER INFORMATION: synthetic real time PCR (RT-PCR) primer
      cyp19a1a fwd

<400> SEQUENCE: 19
ctgctagcca tcagacacca                                                20

<210> SEQ ID NO 20
<211> LENGTH: 20
<212> TYPE: DNA
<213> ORGANISM: Artificial Sequence
<220> FEATURE:
<223> OTHER INFORMATION: synthetic real time PCR (RT-PCR) primer
      cyp19a1a rev

<400> SEQUENCE: 20
atcctgcaac tcctgagcat                                                20
```

MATERNALLY INDUCED STERILITY IN ANIMALS

CROSS-REFERENCES TO RELATED APPLICATIONS

This application is the continuation application of U.S. patent application Ser. No. 13/511,317, filed May 22, 2012, which is the National Stage of International Application No.: PCT/US10/57863, filed on Nov. 23, 2010, and which claims priority to U.S. Provisional Application No. 61/263,468, filed Nov. 23, 2009, the disclosure of each is incorporated herein in its entirety.

STATEMENT AS TO RIGHTS TO INVENTIONS MADE UNDER FEDERALLY SPONSORED RESEARCH AND DEVELOPMENT

This invention was supported in part by government funds under National Institute of Science and Technology Advance Technology Program (NIST-ATP) Agreement #70NANB3H3043 and National Science Foundation SBIR grant #0912837.

REFERENCE TO A "SEQUENCE LISTING", A TABLE, OR A COMPUTER PROGRAM LISTING APPENDIX SUBMITTED ON A COMPACT DISK

This application includes a Sequence Listing as a text file named "086511-002920US-0962220-SEQLIST.txt" created Oct. 28, 2015, and containing 5,408 bytes. The material contained in this text file is incorporated by reference in its entirety for all purposes.

BACKGROUND OF THE INVENTION

There is a need for a technology to control invasive species and pests, e.g., fish, amphibians, mollusks, crustaceans, and insects, that can replace radiation-induced sterile males for mass releases. Reliable sterilization techniques would also be valuable for the application of genetic engineering to beneficial species for improved traits (e.g., disease resistance, improved growth or development, resistance to insecticides, disruption of mechanism for disease transmission).

Traditionally, in commercial aquaculture, sterile fish have been produced by triploid induction (the addition of one extra set of chromosomes). However, triploidy is generally thought to negatively impact performance of many species, and optimal protocols are species dependent. The application of the technology is labor intensive, and it is difficult to guarantee that 100% of the fish are triploid and therefore sterile.

An easier solution would be to mediate sterility with a transgene or mutation. Several transgenic approaches to achieve sterility have been proposed and tested, but as of today, these methods have been at best partially successful. Sterility at the physiological, cellular and molecular level has not been demonstrated (Thresher et al. (2009) *Aquaculture* 290:104-09 and Wong & van Eenennaam (2008) *Aquaculture* 275:1-12).

A major obstacle is the requirement for a temporally reversing sterility to propagate the line. A solution that does not require repeated treatment at each generation would be desirable.

The majority of studies aimed at developing transgenically sterile fish have focused on methods to inactivate hormones involved in gonadal growth, differentiation and maturation. Proposed hormone targets include, the gonadotropin releasing hormone, follicule stimulating hormone, and luteinizing hormone. The silencing of these key genes should in principle lead to sexually immature and sterile fish whose fertility can be rescued by exogenous delivery of the missing hormone.

Although elegant in theory, many difficulties are inherent in this approach. A first problem is the existence of multiple hormone gene family members in some fish genomes. In addition, these hormones have biological function beyond fertility. Finally, in models that rely on knockdown technology, sterility is not 100% and reduction in fertility varies between sex and founder lines.

An alternate approach to silencing endogenous reproduction genes is to create transgenic lines with genes designed to disrupt key signaling pathways in the patterning of early embryonic development, leading to embryo death. This approach uses either gene knockdown technology, such as antisense RNA and dsRNA, or uses the misexpression of a morphogene. These embryonic disrupters are placed under the control of embryonic specific promoters, which are expressed during embryonic development.

To achieve reversibility, and allow propagation of lines, the construct is designed with a bacterial repression system placed between the promoter and the disrupter of the critical development gene. The system uses a commercially available Tet-responsive PhCMV*-11 promoter. In theory, the fish can be bred in captivity if a drug (e.g., tetracycline or a derivative thereof) is applied briefly during embryogenesis blocking the expression of the disrupter gene and providing reversible control over reproduction. To date, efforts to produce sterile lines have proven unsuccessful. Difficulties in creating these lines may be due to leakiness in the Tet responsive promoter, resulting in low levels of expression of the embryonic disrupter gene and subsequent selection against creation of founder lines. The system also requires the use of a bacterial gene and promoter system, which complicates the regulatory review process for commercialization. An additional drawback of this approach is the need to use tetracycline (or its derivatives), which will increase production cost and create environmental hazard.

The present invention addresses many of the drawbacks of earlier methods. The invention provides a transgenic technology platform capable of efficiently sterilizing different species of vertebrate and invertebrate animals. Yet the transgenic line can be easily propagated without use of potentially toxic or harmful agents. The present technology can make commercial production of beneficial species more profitable and environmentally friendly. For example, sterilization of cultured aquatic species will: 1) prevent gene flow to wild populations and colonization of new habitats by cultured non-native species (bioconfinement); 2) protect valuable lines with improved genetics; 3) increase performance by reducing the energy spent on gonad development and sexual differentiation, or by allowing production of all male populations. An all-male population can be advantageous if the males of a species grow faster than females. Sterilization methods that are essentially 100% effective will enable development of transgenic technologies with reduced risk, and promise remarkable improvements over current containment technologies.

Thus, the invention provides significant advantages, including: (i) 100% effectiveness; (ii) lower cost compared to other approaches (no labor or treatment needed to propagate or sterilize the line); (iii) the expressed gene products do not negatively impact host performance or require use of toxin genes or agents with potential health or environmental risks; (vi) broad application of the strategy among different organisms; (vii) broad range of target species using the same construct and (viii) easy propagation of transgenic lines.

BRIEF SUMMARY OF THE INVENTION

The invention provides compositions and methods for generating a transgenic lineage-ending female that will produce a sterile generation of progeny. Also provided are compositions and methods for propagating the transgenic line using transgenic males.

In some embodiments, the invention provides a Maternal Sterility Construct (MSC), i.e., an expression construct comprising: (i) an MSC promoter; (ii) a polynucleotide sequence capable of ablating Primordial Germ Cells (PGCs); and (iii) at least one germ cell specific cis-acting element, wherein (i), (ii), and (iii) are operably-linked. In some embodiments, the MSC promoter is a maternal promoter, e.g., the promoter from the askopos (kop) or zona pellucida (zpc) genes. In some embodiments, the germ cell specific cis-acting element(s) comprise the 3'UTR sequence of a germline gene, e.g., the 3'UTR sequences from the dead-end (dnd) or nanos (nos) genes.

In some embodiments, the polynucleotide sequence capable of ablating PGCs is a pro-apoptotic sequence. In some embodiments, the pro-apoptotic sequence acts directly to apoptose PGCs, and encodes a pro-apoptotic protein such as Bax, Bak, Bok, Bad, Bik, Puma, Noxa, or an effector caspase. In some embodiments, the pro-apoptotic sequence acts indirectly, e.g., by reducing expression of an anti-apoptotic gene, e.g., bcl-2, bcl-xl, bcl-w. In some embodiments, the pro-apoptotic sequences acts indirectly by reducing expression of a gene necessary for proper migration or specification of PGCs, e.g., CXCR4-β, insulin-like receptor 1b, fox c1, or nanos.

In some embodiments, the invention provides transgenic animals carrying the MSC transgene described above. In some embodiments, the MSC transgenic animal is a lineage ending female. In some embodiments, the MSC transgenic animal is selected from the group consisting of: fish, mollusk, crustacean, amphibian, insect, and arthropods. In some embodiments, the MSC transgenic animal carries at least one additional transgene.

In some embodiments, the invention provides methods of producing a lineage ending female, comprising the steps of: (i) introducing an MSC to an animal progenitor cell (e.g., an embryonic cell) to generate a MSC transgenic founder animal carrying the MSC in its germ cells; (ii) breeding the MSC transgenic founder animal from step (i) to produce a hemizygous MSC transgenic male; (iii) breeding the MSC transgenic male with a female lacking the MSC; and (iv) selecting the MSC transgenic female progeny from step (iii) to obtain a lineage ending female. In some embodiments, the method further comprises a step of crossing the lineage ending female from step (iv) to a male to produce a sterile generation of progeny. In some embodiments, the lineage ending female carries at least one additional transgene.

In some embodiments, the invention provides methods of producing a sterile generation of animals, comprising crossing a lineage ending female with a male to produce sterile progeny. In some embodiments, the sterile progeny carry at least one additional transgene.

In some embodiments, only half of the progeny of a lineage ending female inherit the MSC transgene, though all progeny are sterile (FIG. 1). As a population of nontransgenic but sterile animals may have value, in some embodiments, the method further comprises detecting the presence of the MSC transgene and separating the MSC-transgenic sterile progeny from non-MSC-transgenic sterile progeny. In some embodiments, the MSC transgene is detected using a fluorescent marker or a color marker (e.g., by adding an additional coding sequence for the marker to the MSC transgene). In some embodiments, the MSC transgene is detected via death of the MSC-transgenic sterile progeny (e.g., by adding a lethal coding sequence to the MSC transgene under the control of a conditional or developmental stage-specific promoter).

In some embodiments, the invention provides methods of propagating MSC transgenic animals, comprising: (i) introducing an MSC to an animal progenitor cell to generate a MSC transgenic founder animal carrying the MSC in its germ cells; (ii) breeding the MSC transgenic founder animal from step (i) to produce a hemizygous MSC transgenic male; (iii) breeding the MSC transgenic male with a female lacking the MSC; and (iv) selecting the MSC transgenic male progeny from step (iii) to breed and propagate another generation of MSC transgenic animals.

Also provided herein is a method of propagating Maternal Sterility Construct (MSC) transgenic male fish. The method includes (i) obtaining a MSC comprising: (a) a promoter that is specifically active in a developing oocyte during oogenesis; (b) a polynucleotide sequence that ablates primordial germ cells (PGCs) after fertilization of the oocyte; and (c) a germ cell specific 3' untranslated region (UTR), wherein (a), (b), and (c) are operably linked; (ii) introducing the MSC to a fish embryo to generate a male MSC transgenic founder fish carrying the construct in its germ cell; (iii) identifying and breeding the MSC transgenic male founder fish from step (ii) to produce a hemizygous MSC transgenic male fish carrying the construct in its germ cell; (iv) breeding the hemizygous MSC transgenic male fish with a female fish of same species lacking the MSC; and (v) selecting a hemizygous MSC transgenic male progeny from step (iv). In some embodiments, the method further comprises breeding the hemizygous MSC transgenic male progeny from step (v) with a female fish of same species lacking the MSC to propagate a line of hemizygous MSC transgenic male fish. In other embodiments, the method also includes selecting a MSC transgenic female progeny from step (iv) to obtain a lineage ending female fish that expresses MSC and is fertile. In some instances, the lineage ending female fish carries at least one additional non-MSC transgene. In some embodiments, the MSC transgenic male founder fish of step (ii) carries at least one additional non-MSC transgene. The hemizygous MSC transgenic male fish of step (iii) can carry at least one additional non-MSC transgene.

In another aspect, the present disclosure provides a method of generating a sterile fish from a lineage ending female fish comprising crossing the lineage ending female fish described herein with a male fish of the same species that lacks the MSC.

BRIEF DESCRIPTION OF THE DRAWINGS

FIG. 1: Flowchart portraying an example of generating sterile animals and propagating an MSC transgenic line.

DETAILED DESCRIPTION OF THE INVENTION

I. Introduction

Figure 2:
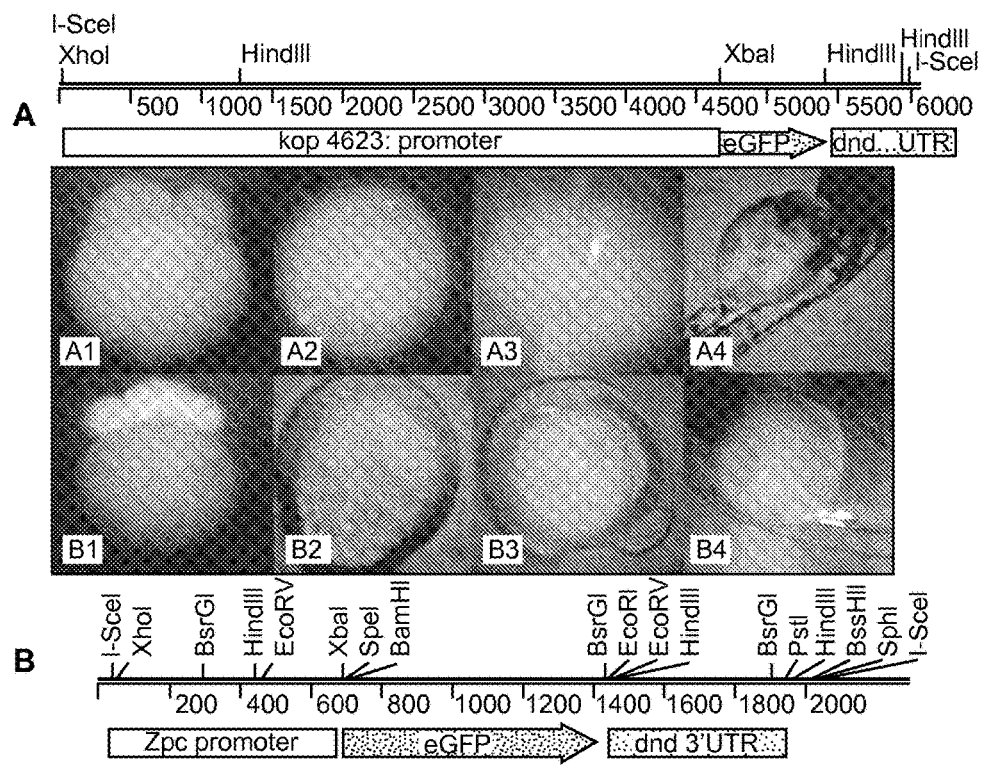
FIG. 2: Early labeling of PGCs in live embryos from transgenic females carrying the transgenes. (A) askopos: eGFP-dnd 3'UTR; or (B) zpc: eGFP-dnd 3'UTR. The embryos result from transgenic females crossed with wild type males. GFP is evenly distributed into the blastodisk until the oblong stage (A and B 1-2). The earliest time point when the germ cells can be distinguished from somatic cells is during early gastrulation (4 hours post fertilization, A2 and B2). A3, B3: embryos in late somatogenesis, and A4, B4: embryos 30-48 hrs post fertilization (hpf).

The invention provides compositions and methods for creating sterile animals in an economically efficient way. The technology uses spatial- and temporal-specific delivery of a transgene product that eliminates the Primordial Germ Cells (PGCs) in a developing embryo. Without germ cells, the embryos mature into sterile animals. The sterility-inducing transgene is a Maternal Sterility Construct (MSC) that requires three elements: an MSC promoter driving a polynucleotide sequence capable of ablating PGCs, fused to germ cell specific cis-regulatory elements (e.g., 3'UTR). The presence of the MSC transgene in a female will cause her progeny to be sterile, regardless of whether the male parent carries the MSC transgene. MSC transgenic males can be crossed with wild-type females to propagate the line, and these progeny are not sterile.

FIG. 1 illustrates how the MSC transgene can either be maintained, or used to produce sterile animals. In Step 1, the transgene is introduced into progenitor cells (e.g., embryonic stem cells) to produce an MSC transgenic founder animal. Founder animals capable of germ line transmission of the MSC transgene are crossed to an MSC negative animal to generate an F1 generation of MSC transgenic animals (Step 2). Presence of the transgene in the offspring can be detected according to standard methods, e.g., PCR, or addition of a gene encoding a readily visible trait to the MSC.

Hemizygous MSC transgenic males are used to propagate the line (Step 3). This is because the sequence capable of ablating PGCs is not expressed in male germ cells. The progeny of MSC transgenic males develop germ cells normally and are fertile.

Females that carry the MSC transgene are lineage ending females. As explained and illustrated herein, the PGC-ablating sequence is expressed in the mother's germ cells from the oocyte-specific promoter. The PGC-ablating product is passed on to her progeny, resulting in offspring with no germ cells. The lineage ending female will produce sterile offspring independent of the MSC status of the father. The offspring of a lineage ending female will be sterile if they are MSC negative, hemizygous, or homozygous.

More particularly, the disclosed system allows spatial and temporal control of expression of the pro-death polynucleotide sequence first in the oocyte and later in PGCs (in the developing embryo derived from the same egg). Oocyte apoptosis is regulated by multiple pro- and anti-apoptotic signaling pathways (see, e.g., Morita et al. (2000) *Nat. Med.* 6:1109-14; Sasaki and Chiba (2004) *Mol. Biol. Cell* 15:1387-96; Andersen et al. (2009) *EMBO* 28:3216-27). Oocytes are more resistant to apoptosis than many cell types, and ectopic overexpression of bax alone is not sufficient to promote oocyte apoptosis. Thus, the transgene can be expressed in both cell types, but only result in ablation of PGCs.

Pro-apoptotic activity can be further limited to the PGCs with cis-acting RNA elements that reside in the 3'UTR of germ plasm RNA. These elements target RNA translation to the PGCs. First, they allow localization of the mRNAs to a specialized cytoplasmic region called the germ plasm. This region is inherited by future PGCs and necessary for their specification (Yoon (1997) *Development* 124:3157-65; Koprunner et al (2001) *Genes & Dev.* 15:2877-85; Weidinger et al. (2003) *Cur. Biol.* 13; 1429-34). Second, they inhibit productive translation of mRNAs that fail to properly localize and migrate to somatic cells. Third, they allow rapid degradation of the mRNA in somatic cells while stabilizing those same mRNA in PGCs (Wolke et al. (2002) *Cur. Biol.* 12:289-94).

The evolutionarily conserved nature of the machinery responsible for maternal germ cell mRNA translation within PGCs makes the use of germ cell 3'UTR particularly attractive for the delivery of specific heterologous mRNA to PGCs, and allows application of this approach to a broad range of host target species.

The present invention provides an effective means for population containment. In the case of farmed species, MSC transgenic females can produce multiple generations of sterile progeny, while MSC transgenic males can be used to propagate a fertile MSC transgenic population. For invasive and pest species, a one-time release of fertile MSC transgenic males into the population can result in marked depletion or eradication within a few generations, depending on the number of individuals released and the size of the endogenous population. In this situation, the MSC transgenic males carry the "Trojan gene," allowing continuous generation of MSC transgenic females and thus continuous production of sterile males. Sterile males compete with non-transgenic males for females, and the next generation is reduced in size. A similar result can be achieved using mass release of sterile males, e.g., sterile offspring of an MSC transgenic female. The mass release of sterile males has been used successfully to reduce the population of several insect species (e.g., Screw-worm fly, Medfly) using irradiation as the sterilization method (Sterile Insect Technique or SIT).

II. Definitions

As used herein, an "expression construct" broadly refers to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

A "maternal sterility construct" (MSC) refers to an expression construct that confers sterility on the progeny of a fertile female animal that carries the MSC in her germ cells. The MSC comprises three elements: an oocyte-specific promoter that drives expression of a polynucleotide sequence capable of ablating PGCs (e.g., a pro-apoptotic sequence), and at least one germ cell-specific cis-acting element such as those present in the 3' UTR of germ cell specific genes. The cis-acting element(s) in the 3'UTR of germ cell specific genes direct the mRNA to the germ plasm in the oocyte/zygote, and then to PGCs. The presence of the MSC in the female germ cell causes apoptosis in the primordial germ cells (PGCs) of her progeny, resulting in a sterile generation.

A "promoter" is broadly defined as a nucleic acid control sequences that directs transcription of a nucleic acid. A promoter can include necessary nucleic acid sequences near the start site of transcription, such as, in the case of a polymerase II type promoter, a TATA element. Promoters can be constitutive, inducible, or tissue-specific.

An "MSC promoter" drives expression of an operably-linked polynucleotide sequence during oogenesis. There are two types of MSC promoters: i) promoters of maternal genes and ii) promoters for oogenesis. Maternal genes (such as vasa and askopos) are expressed during oogenesis by the mother, and the gene products (mRNA and protein) are deposited in or retained in the mature egg. Maternal gene products are involved in cell fate decisions and basic cellular functions in early development. Promoters for oogenesis (e.g., the zona pellucida promoter) are expressed during oogenesis, but associated gene products are not necessary for early embryo function. As used herein, MSC promoters can also include those from insect nurse cells. In some insect species, oocytes are connected to nurse cells, which provide a significant amount of RNA and protein to the oocyte via cytoplasmic bridges.

A "polynucleotide sequence capable of ablating Primordial Germ Cells" (PGCs) refers to a polynucleotide sequence that, upon expression from an MSC, results in death of PGCs. Such polynucleotides can act directly, e.g., by encoding a pro-apoptotic gene such as bax. The polynucleotide can also act indirectly. In some embodiments, the polynucleotide sequence includes antisense or inhibitory polynucleotides (e.g., siRNA or dsRNA) that specifically reduces expression of an anti-apoptotic gene such as bcl-2. PGCs can also be indirectly eliminated by blocking proper migration or development, which results in apoptosis. Thus, polynucleotide sequences that are capable of ablating PGCs include, e.g., polynucleotides to reduce expression of chemokine receptors and those encoding dominant negative chemokine receptors.

A "pro-apoptotic polynucleotide sequence" refers to a polynucleotide sequence that, when expressed in a cell, causes apoptosis in the cell. The pro-apoptotic polynucleotide sequence can comprise a coding sequence for a pro-apoptotic factor (e.g., Bax), or an inhibitory polynucleotide sequence for an anti-apoptotic factor (e.g., Bcl-2).

A "germ cell-specific cis-acting element" or "germ cell-specific 3' UTR" is an untranslated stretch of transcribed sequence that physically directs the transcript to a part of the cell that is passed to PGCs. For example, a transcript comprising a germ cell-specific 3' UTR, and produced in an oocyte, will be directed to a part of the cytoplasm (the germ plasm) that is inherited by future PGCs. It is possible to create synthetic 3'UTRs or use novel combinations of germ cell specific cis-acting elements from different 3'UTR origins to achieve the same effect.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The phrase "a nucleic acid sequence encoding" refers to a nucleic acid which contains sequence information for a primary amino acid sequence of a specific protein or peptide, an inhibitory polynucleotide sequence that specifically inhibits expression of a particular gene, or a binding site for a trans-acting regulatory agent. This phrase specifically encompasses degenerate codons (i.e., different codons which encode a single amino acid) of the native sequence or sequences which may be introduced to conform with codon preference in a specific host cell.

An inhibitory polynucleotide sequence is one that inhibits expression of a specific targeted gene Inhibitory polynucleotides include antisense constructs or constructs expressing inverted sequences (e.g., siRNA, shRNA) and aptamers, as described in more detail below.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, a recombinant expression vector can include sequence elements that are not found in proximity in a non-recombinant cell.

A "lineage ending female" is an animal that carries an MSC transgene in her germ cells. The progeny of the lineage ending female are sterile.

The term "transgenic animal" refers to an animal that carries a heterologous polynucleotide sequence (transgene) in its genome that is purposefully introduced by recombinant techniques familiar in the art. Transgenes generally include sequence elements that allow insertion into the genome of the host organism, a promoter and/or other expression element, a gene or cDNA sequence that encodes a protein or a sequence that inhibits expression of another gene (e.g., an antisense sequence).

A "founder animal" refers to a first generation animal resulting from recombinant introduction of a transgene into an embryonic or other progenitor cell. In most cases, such animals are mosaic, so that only some of the cells are derived from the transgenic cell. It is possible, however, to create an animal from a single cell or population of cells that all include the transgene. If the founder animal is "germ-line transformed," or carries the transgene in its germ cells, it can produce transgenic offspring.

The terms "hemizygous" and "homozygous" are used to refer to diploid organisms, and can refer to transgenic animals. As used herein, a hemizygous transgenic animal carries one copy of the chromosome where the transgene inserted, but the matching chromosome does not have the transgene. In some cases, the term heterozygous is used interchangeably with hemizygous when referring to an animal carrying one copy of a transgenic chromosome. In an animal that is homozygous for the transgene, both copies of the chromosome include the transgene, so that the animal carries two copies of the transgenic chromosome.

As used herein, the term "wild-type" generally refers to an animal that does not carry the MSC transgene.

The term "sterile" refers to an individual or population of individuals with significantly diminished ability to generate offspring as compared to normal individuals of the same age, species, etc.

The terms "inhibit" or "activate" or "modulate," when referring to expression or activity, are not intended as absolute terms. For example, if an agent "does not inhibit" or "does not activate" a given activity, it generally means that the agent does not have a significant effect, e.g., as compared to a control or range of controls. The terms "reduce," "induce," and "increase" and similar relative terms are used herein to refer to reductions, increases, etc. relative to a control value. Those of skill in the art are capable of determining an appropriate control for each situation. For example, if an agent is said to inhibit expression of gene X, the level of X expression in the presence of the agent is reduced compared to the level in the absence of the agent. If an agent is said to induce sterility in a given population, the level of sterility will be increased in the presence of the agent compared to the level in the absence of the agent.

A "control" sample or value refers to a sample or set of conditions that serves as a reference, usually a known reference, for comparison to a test sample. For example, a control sample appropriate in the present invention can be, e.g., gonads or gonadal cells from a wild type animal. Such a control can then be compared to a sample obtained from an animal carrying an MSC transgene or a component thereof, or an animal suspected of carrying an MSC transgene or a component thereof. A control can also represent an average value gathered from a population of similar individuals, e.g., wild type animals with a similar profile, age, weight, etc. One of skill in the art will recognize that controls can be designed for assessment of any number of parameters. Controls can also be designed for in vitro applications, e.g., testing the activity of various constructs in cultured cells.

III. Recombinant Techniques

The invention involves routine techniques in the field of recombinant genetics, e.g., for the preparation of MSCs. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999).

Eukaryotic and prokaryotic cells can be used for routine cloning and expression. These include animal cells, insect cells, bacteria, fungi, and yeasts, many of which are commercially available. Methods for introduction and expression of isolated or heterologous nucleic acids in a cell are well-known, and can be found, for example, in the general reference, supra. Accordingly, this invention also provides for host cells and expression vectors comprising the nucleic acid sequences described herein.

Nucleic acids including MSCs and MSC components (described in more detail below) can be made using standard recombinant or synthetic techniques. Nucleic acids may be RNA, DNA, or hybrids thereof. One of skill can construct a variety of clones containing functionally equivalent nucleic acids, such as nucleic acids that encode the same polypeptide. Cloning methodologies to accomplish these ends, and sequencing methods to verify the sequence of nucleic acids are well known in the art.

In some embodiments, the nucleic acids are synthesized in vitro. Deoxynucleotides may be synthesized chemically according to the solid phase phosphoramidite triester method described by Beaucage & Caruthers, *Tetrahedron Letts.* 22(20):1859-1862 (1981), using an automated synthesizer, e.g., as described in Needham-VanDevanter, et al., *Nucleic Acids Res.* 12:6159-6168 (1984). In other embodiments, the desired nucleic acid sequence may be obtained by an amplification reaction, e.g., PCR.

One of skill will recognize many other ways of generating alterations or variants of a given polynucleotide or polypeptide sequence. A desired nucleic acid or polypeptide of the invention based upon the sequences referred to herein and the knowledge readily available in the art regarding pro- and anti-apoptosis factors, tissue specific promoters and cis-acting elements.

To obtain high level expression of a desired sequence (e.g., a sequence that results in ablation of PGCs), an expression vector is constructed that includes such elements as a promoter to direct transcription, a transcription/translation terminator, a ribosome binding site for translational initiation, and the like. Suitable bacterial promoters are well known in the art and described, e.g., in the references providing expression cloning methods and protocols cited hereinabove. Bacterial expression systems for expressing ribonuclease are available in, e.g., *E. coli, Bacillus* sp., and *Salmonella* (see, also, Palva, et al., *Gene* 22:229-235 (1983); Mosbach, et al., *Nature* 302:543-545 (1983). Kits for such expression systems are commercially available. Eukaryotic expression systems for mammalian cells, yeast, and insect cells are well known in the art and are also commercially available.

In addition to the promoter, the expression vector typically contains a transcription unit or expression cassette that contains all the additional elements required for expression of the nucleic acid in host cells. A typical expression cassette thus contains a promoter operably linked to the nucleic acid sequence encoding the protein or inhibitory polynucleotide, and signals required for efficient polyadenylation of the transcript, ribosome binding sites, and translation termination.

As noted above, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET15b, pET23D, pET-22b(+), and fusion expression systems such as GST and LacZ. Epitope tags can also be added to recombinant proteins to provide convenient methods of isolation, e.g., 6-his. These vectors comprise, in addition to the expression cassette containing the coding sequence, the T7 promoter, transcription initiator and terminator, the pBR322 ori site, a bla coding sequence and a lacI operator.

The vectors comprising MSC nucleic acid sequences can be expressed in a variety of host cells, including *E. coli*, other bacterial hosts, yeast, and various higher eukaryotic cells such as the COS, CHO and HeLa cells lines and myeloma cell lines. In addition to cells, vectors can be expressed by transgenic animals.

The expression vectors or plasmids of the invention can be transferred into the chosen host cell by well-known methods such as calcium chloride transformation for *E. coli* and calcium phosphate treatment, liposomal fusion or electroporation for mammalian cells. Cells transformed by the plasmids can be selected by resistance to antibiotics conferred by genes contained on the plasmids, such as the amp, gpt, neo and hyg genes.

The expression level of a gene can be determined by detecting mRNA, protein, or activity according to techniques known in the art. For example, mRNA levels can be detected using Northern blots, reverse transcription PCR (RTPCR), or quantitative RTPCR (sometimes called real time PCR). Such techniques are reviewed, e.g., in VanGuilder et al. (2008) *Biotechniques* 44:619 and *Real-Time PCR: Current Technology and Applications*, Caister Academic Press (2009). Protein levels can be detected using antibody-based assays, e.g., Western blots or ELISAs. In some embodiments, protein expression can be detected by detecting an operably-linked protein label, e.g., GFP, 6-histine, or biotin.

IV. Inhibitory Nucleic Acids

Inhibitory nucleic acids include those based on antisense technology and Watson-Crick pairing, as well as aptamers. Aptamers are short sequences (usually 20-200 bases in length) that bind to a targeted molecule via non-Watson-Crick interactions, and can include modified nucleic acids. The design and selection of target-specific aptamers is known in the art, e.g., as described in U.S. Pat. Nos. 5,270,163, 5,567,588, and 5,475,096, and Klug and Famulok (1994) *Mol. Biol. Reports* 20:97-107. Aptamers can be designed to selectively bind to and inhibit an anti-apoptotic polypeptide, similar to an antibody, according to known methods.

An "antisense nucleic acid" is a non-enzymatic nucleic acid molecule that binds to target RNA by means of RNA-RNA or RNA-DNA or RNA-PNA interactions and alters the activity of the target RNA (for a review, see Stein and Cheng (1993) Science 261:1004 and Woolf et al., U.S. Pat. No. 5,849,902). Typically, antisense molecules are complementary to a target sequence along a single contiguous sequence of the antisense molecule. For a review of antisense strategies, see Schmajuk et al. (1999) *J. Biol. Chem.*, 274, 21783-21789, Delihas et al. (1997) Nature, 15, 751-753, Stein et al. (1997) *Antisense N. A. Drug Dev.*, 7, 151, Crooke (2000) *Methods Enzymol.*, 313, 3-45; Crooke (1998) *Biotech. Genet. Eng. Rev.*, 15, 121-157, Crooke (1997) *Ad. Pharmacol*, 40, 1-49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Small interfering RNA (siRNA) can be used to inhibit expression of an anti-apoptotic gene. siRNA targeted against HIV-1 rev transcripts has been successful in human cells (*Nature Biotechnol.* 20:500-505; Miyagishi M, and Taira K. (2002)). U6-promoter-driven siRNAs with four uridine 3' overhangs efficiently suppress targeted gene expression in mammalian cells (*Nature Biotechnol.* 20:497-500; Paddison et al. *Genes & Dev.* 16:948-958; Paul et al. (2002) *Nature Biotechnol.* 20:505-508; Sui et al. (2002) *Proc. Natl. Acad. Sci. USA* 99(6):5515-5520; Yu (2002) *Proc. Natl. Acad. Sci. USA* 99(9):6047-6052.

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression. The term "double stranded RNA" or "dsRNA" as used herein refers to a double stranded RNA molecule capable of RNA interference "RNAi", including short interfering RNA "siRNA" (see, e.g., WO 00/44895; WO 01/36646; WO 01/29058; WO 00/44914).

An inhibitory nucleic acid molecule of the instant invention can be between about 10 and 100 nucleotides in length. For example, RNAi nucleic acid molecules of the invention can be between about 15 and 50 nucleotides in length, more preferably between about 25 and 40 nucleotides in length (for example see Jarvis et al. (1996) *J. Biol. Chem.*, 271, 29107 29112). Those skilled in the art will recognize that all that is required is that the nucleic acid molecule be of sufficient length and suitable conformation for the nucleic acid molecule to interact with its target.

V. Transgenic Techniques

Methods of generating transgenic animals are known for a number of species. General references include: *Transgenesis Techniques: Principles and Protocols*, Clarke ed. 2002; *Germ Cell Protocols: Sperm and Oocyte Analysis*, Schatten ed. 2004; and *Fish Development and Genetics: The Zebrafish and Medaka Models*, Gong & Korzh ed. 2004.

Briefly, an expression construct comprising a transgene is introduced into a cell capable of giving rise to an animal, such as a sperm cell, an embryonic stem cell, or other progenitor cell. This can be accomplished using, e.g., microinjection or electroporetic techniques. The transgene-carrying progenitor cell (or cells) is then cultured to produce an animal carrying the transgene.

In most cases, the founder animal will carry the transgene in only some of the cells, such that the animal is a genetic mosaic. However, in some methods, an animal can be grown directly from a single progenitor cell that is stably transformed to carry the transgene. In the latter case, the animal will not be mosaic. The founder animal is often referred to as the F0 generation. The founder animals are crossed, and assuming germline transformation of the founder, will generate the F1 generation, with some of these progeny carrying the transgene.

Methods for generating transgenic fish are disclosed, e.g., in Mori & Devlin (1999) *Mol. Cell. Endocrin.* 149:129 and Collas & Alestrom (1997) *Mol. Mar. Biol. Biotechnol.* 6:48-58. Transgenic transformation of insects is described, e.g., Kaiser & Goodwin (1990) *Proc. Natl. Acad. Sci. USA* 87:1686-90. Methods of generating transgenic mollusks are disclosed, e.g., in Boulo et al. (1996) *Mol. Mar. Bio. Biotechnol.* 5:167-74. Methods for generating transgenic arthropods can be found, e.g., in Presnail & Hoy (1992) *Proc. Natl. Acad. Sci. USA* 89:7732-36. Methods of generating transgenic amphibians (Xenopus) are disclosed in Beck et al. (2001) *Genome Biol.* 2:1029.

The presence of the MSC transgene can be tracked by direct detection of the transgene, e.g., using standard PCR or hybridization techniques specific for transgenic sequences. As with the examples described herein, primers specific for the junction between bax and dead-end 3'UTR can be used. This junction does not exist in the wild type fish genome. The transgene can also be designed to include a dominant gene marker encoding a readily detestably label or trait. For example, genes that affect color, pigmentation, or body shape, or that allow for conditional selection, can be used.

One approach is a selective process resulting in the removal (death) of individuals carrying the dominant gene linked with the MSC. For example, application of a stimulus or stress resulting in the death of individual carrying the dominant gene or removal of a stimulus/condition required for maintenance of the transgene. Another method for selecting transgenics can be performed using fluorescent screening technique, whereby the dominant gene expresses fluorescent proteins to enable the identification of individuals carrying the transgene.

VI. MSC Promoter

MSC promoters that can be used according to the invention are those which are active during oogenesis. The choice of the promoter for the MSC can determine the ease and effectiveness of the MSC in generating lineage ending females and sterile progeny. Promoters that drive expression of maternally provided transcripts (promoters of maternal genes), that are produced during oogenesis and present in the egg at fertilization, can be used to target PGCs in early embryos. Additional promoters (promoters for oognosis) which can be used according to the invention are those which are specifically active in oocytes during oogenesis, and whose product is not required for embryonic development. A useful MSC promoter i) has promoter activity restricted to females, ii) is active during oogenesis, and iii) in preferably not active elsewhere spatially or temporally in the animal.

The products of maternal genes (mRNA and protein) are stored in the mature eggs where they are involved in cell-fate decisions and basic cellular functions in early development.

These gene products are generally active prior to the activation of the zygotic genome at the midblastula transition (Kane and Kimmel (1993) *Dev.* 119:447-56). Strictly maternal genes are expressed during oogenesis and this maternal expression is both required and sufficient to carry out all the function of the gene in the early embryo. Strictly maternal genes therefore function independently of the genotypes of the embryo and father. In zebrafish, this category of genes includes genes such as futile cycle, janus, nebel, and ichabod.

An MSC promoter, linked to the appropriate 3' UTR, that is temporally and spatially restricted to the oocyte is advantageous because: 1) maternal contribution of the transcripts to the oocytes targets PGCs early during embryonic development, when the PGC population is small, and can be completely eliminated and 2) female-only transgene expression allows propagation of the sterile line via the transgenic males. Transgenic males carrying the MSC will not express the transgene and remain fertile. This approach therefore eliminates the need for some mechanism to reverse sterility. Because the expression of the transgene takes place in the oocytes before meiosis has occurred, the transgene product will be present in all eggs produced by heterozygous transgenic females. While only half of the progeny of the MSC female inherit the transgene, all progeny will be sterile.

The examples below describe use of the regulatory upstream region of the maternal-specific gene askopos (4.623kb:kop) and oogenesis-specific gene zona pellucida (634 bp:zpc3b) for use in the MSC (Baler et al. (2005) *J. Cell Sci.* 118:4027-38; Onichtchouk et al. (2003) *Dev. Dynamics* 228:393-404).

Several other candidate gene promoters can be used to achieve maternal expression, including promoters of other germ plasm specific genes. Oogenesis-specific promoters such as zorg and OORP-T (Dai et al. (2009) *Theriogenology* 71:441-49; Ramachandra et al. (2007) *Mol. Reprod. Dev.* 74) can also be used.

In *Drosophila*, examples of promoters of maternal genes include those from the bicoid, hunchback, nanos and caudal genes. These genes participate in the establishment of axes and germ line. In zebrafish, maternal specific genes governing development have been identified through either functional genetic screen or by in situ hybridization, followed by knock down analysis of the gene function (e.g., askopos).

A broad category of promoters of maternal genes can be obtained from genes which have been more extensively studied in invertebrates and vertebrates. These are germ line-specific genes whose mRNA are found in the germ plasm, and include: nanos, dead-end (dnd), DazL, GasZ, granulito, tudor, Bruno-like, vasa, oskar, tudor (TDR7), ziwi, zorg, germ-cell-less (gcl) (Strasser et al. (2008) *BMC Dev. Biol.* 8:58; Suzuki et al. (2000) *Mech. Dev.* 93:205-09).

In *Anopheles gambiae*, the vasa promoter has been characterized (Papathanos et al. (2009) *BMC Mol. Biol.* 10:65) and the study of a crustacean vasa protein supports maternal contribution. In Xenopus, maternal genes include those coding for Vg-1 and VegT, Xcat2, Xpat, and Xdaz1.

Additional promoters for oogenesis which can be used according to the invention are those which are specifically active in oocytes during oogenesis and whose product is not required for embryonic development. Many genes within this category are under the control of a single promoter and encode proteins which are vital for oogenesis, ovarian folliculogenesis and fertilization such as, for example, Zona pellucida proteins, OORP-T, Factor in Germline alpha (FIGLa), Growth Factor 9 (GDF9), and Bone Morphogenetic-Protein 15 (BMP-15). Promoters from the zona pellucida (zpc) gene family can be used. Transgenic zebrafish containing stably integrated copies of zebrafish zpc3 promoters linked to the green fluorescent protein (GFP) have been generated, and result in GFP expression in a pattern resembling that of endogenous zpc genes. The first transgenic line used 412 by of sequence upstream of the ATG codon of a single-copy zpc3 homologue (Onichtchouk D. et al., 2003; Del Giacco L. et al., 2000)) (Liu X. et al., 2006). The conserved CCAAT sequence elements of the tandemly arrayed zebrafish zpc2 and zpc3 genes are necessary for this expression in developing oocytes (Mold et al., 2009). Another category of genes includes those that switch from somatic promoter to an oogenesis promoter, such as the Xenopus TFIIIA gene, which is transcribed from separate promoters in oocyte and somatic tissue (Kim et al. (1990) *Genes Dev.* 4:1602).

The sequences referred to herein have been characterized for many species, and the sequences are publically available, e.g., on Genbank. One of skill can determine which sequence (e.g., species homologs, slight variants) can be used advantageously in each situation without undue experimentation.

The ability of a candidate promoter to direct gene expression at a particular stage can be determined according to methods known in the art, e.g., such as by the methods disclosed in the above references. Ideally, the identity of the cell (e.g., lineage and developmental stage) is simultaneously detected with a known cell marker. For example, PGCs can be labeled with a GFP-expressing construct as described in the examples (zpc promoter—egfp—dnd 3'UTR). One can detect expression of a transcript or protein product downstream of the candidate promoter using standard molecular biological techniques, e.g., RTPCR, qRT-PCR, Northern or Western blots. Alternatively, the transcript or protein product can be detected microscopically, using a detectably labeled probe or antibody. For example, a candidate promoter can be linked to a sequence encoding GFP or similar fluorescent protein, and inserted into a population of cells, such as oocytes. Expression from the promoter can then be tracked and compared, e.g., to expression from a known promoter.

VII. Polynucleotide Sequences Capable of Ablating Primordial Germ Cells

The invention includes a PGC-ablating element expressed in PGCs. However, expression can also occur in oocytes and early embryos (as illustrated with the reporter gene construct in FIG. 2, A1-2 and B1-2, and FIG. 3). In order to specifically ablate only PGCs, the effector gene should have no or only limited effect on oocytes and somatic cells in early embryos. With this in mind, apoptotic gene regulators are of particular interest in our system because oocytes and embryos before gastrulation are naturally resistant to apoptosis.

The polynucleotides and polypeptides referred to herein have been characterized for many species, and the sequences are publically available, e.g., on Genbank. One of skill can determine which sequence (e.g., species homologs, slight variants) can be used advantageously in each situation without undue experimentation. For example, a publically available database describing Bcl-2 family members can be found at bcl2db.ibcp.fr/site/.

The studies described herein rely on bax as the gene for promoting apoptosis in PGCs. Substitute proapoptotic genes include other members of the bax family such as bak and bok and those including the class of BH3-only proteins such as Bad, Bik, Puma and Noxa. In preliminary experiments, we found that zbik-dnd 3'UTR mRNA can induce disappearance of GFP-labeled PGCs in embryos 24 hours post injection, similar to that observed in experiments performed with bax-dnd 3'UTR mRNA.

Apoptosis is carried out by the activation of downstream caspases. Conversion of an inactive procaspase into an effector caspase induces specific substrate cleavage, activation of DNAses, and the demolition of the cell. Thus, effector caspases can be used according to the invention to specifically ablate PGCs. However, if the resistance of oocytes and early embryonic somatic cells to apoptosis derives from an earlier step in the pathway (e.g., prior to cytochrome c release), there is a risk that these cells will also undergo apoptosis.

Apoptosis is regulated by the balance between pro- and anti-apoptotic molecules. The apoptotic threshold of a cell can be breached through either increased expression of pro-apoptotic or decreased expression of pro-survival genes. As such, targeted down-regulation of anti-apoptotic genes such as bcl-2, bcl-xl, or bcl-w, can also lead to cell death. Targeted down-regulation of anti-apoptotic genes can be achieved using inhibitory nucleic acids (e.g., antisense). Anti-apoptotic Bcl-2 family proteins can form heterodimers with bax and other pro-apoptotic proteins, and function upstream of the apoptotic pathway. This approach is therefore preferable to the pro-caspase gene strategy for preserving non-PGCs.

Ablation of primordial germ cells can be achieved indirectly through alteration of the mechanism involved in their migration or specification. During normal migration, germ cells that migrate improperly die because they fail to reach regions of the embryo that permit survival. The molecule responsible for attracting zebrafish PGCs towards the future gonad is SDF-1α, a chemokine secreted by somatic cells. PGCs express the corresponding receptor, CXCR4β. Downregulation of the receptor by an oocyte-specific promoter will alter PGC migration and lead to the activation of apoptosis in these cells. Again, down-regulation of specific genes in PGCs can be achieved using inhibitory nucleic acids such as antisense. No additional protein is expressed in antisense approaches, thus, the regulatory review process might be facilitated. Success of this strategy depends on the absence of redundant or additional function performed by the down-regulated gene during early development. Other genes implicated in PGC migration, and useful for the present invention, include ggt1, hmgcr and dead-end. Genes implicated in PGC specification include, e.g., vasa and nanos.

Another strategy for ablating PGCs is the expression of a dominant negative mutant allele of the c-kit membrane receptor or CXCR4β (Fleischman (1992) *J. Clin. Invest.* 89:1713; Spritz et al. (1992) *Am. J. Hum. Genetics* 50:261). Dominant negative receptor expression in PGCs would disrupt steel growth factor and SDF-1α mediated signaling, respectively.

The ability of a candidate PGC-ablating element to cause cell death in PGCs can be tested according to known methods. The candidate PGC-ablating polynucleotide sequence can be expressed in vitro in a population of PGCs and compared to: (i) a population of PGCs without the expression and/or (ii) a population of PGCs expressing a sequence known to cause cell death in PGCs, e.g., bax.

Cell death by apoptosis is generally detectable using a microscope to observe the cells. Apoptosis causes several uniquely recognizable effects in cells: shrinkage, bubble-like blebs on the surface, chromatin degradation, mitochondrial breakdown and cytochrome c release, breakage into small membrane-enclosed fragments, phosphatidylserine is exposed on the cell surface. Inflammation is inhibited by local phagocytic cells that secrete, e.g., IL-10 and TGF-β. Many of these apoptotic signs can be readily observed, and commercially available kits can also be used for detecting apoptosis, e.g., ELISAs and TUNEL assay kits.

VIII. Germ Cell-Specific 3'UTR

Cis-acting elements can determine localization of a transcript in the cytoplasm before translation is initiated. These cis-acting elements are commonly located in the 3'untranslated region (3'UTR). Sequences in the 3'UTR are recognized and directed accordingly, e.g., by molecular motors or sequestering proteins. A review of cis-acting elements can be found, e.g., in Jambhekar et al. (2007) *RNA* 13:625-42.

One of the first recognized examples of this phenomena was the Drosophila bicoid protein. Bicoid transcripts are directed to one end of a developing oocyte, and upon translation, bicoid is localized to the anterior portion of the cell. This allows for proper localization of bicoid activity for head and thorax formation in the developing embryo.

Certain 3'UTR elements are involved in mRNA localization in oocytes, and direct transcripts to the germ plasm, which develops into primodial germ cells. These elements are germ cell specific 3'UTRs. The sequences of germ cell specific 3'UTRs are highly conserved evolutionarily among animals where the germ cells are specified by a maternally-inherited determinant, i.e., preformation (see Extravour and Akam (2003) *Development* 130:5869-84). The 3'UTR of the zebrafish dead-end (dnd 3'UTR) and nanos1 genes (nanos 3'UTR) can be used to achieve specific expression in PGCs. In zebrafish, both genes were originally identified as a maternal mRNA that localized to primodial germ cells (Koprunner et al. (2001) *Genes & Dev.* 15:2877-85; Weidinger et al. (2003) *Curr. Biol.* 13:1429-34). This localization was presumably through the action of a cis-acting RNA element in their 3'UTR.

In addition to those of dead-end and nanos, several other 3'UTR belonging to germ plasm specific mRNAs can be used in this system. These include that of DazL, GasZ, vasa, tudor7, bruno-like, and granulito.

Translational repression and differential stability of germ plasm RNA are tuned by microRNA and repressors of microRNA. Together with cis-acting motifs in the 3'UTR of germ plasm RNA, microRNA and its repressors have been found to be evolutionary conserved and functionally interchangeable across lower vertebrates ranging from fish to frogs (Knaut et al. (2002) *Cur. Biol.* 12:545-66).

Given the highly conserved nature of germ cell specific cis-acting elements, these sequences can be synthetically designed, e.g., from fragments of known elements. Any non-translated region that directs mRNA transcripts to the germ plasm or PGC can be used according to the methods of the invention.

Germ cell specific localization activity can be detected according to known methods. For example, the localization of an mRNA transcript comprising a candidate germ cell specific cis-acting element can be detected using hybridization techniques, e.g., with a detectably labeled oligonucleotide probe specific for a subsequence of the mRNA transcript. Alternatively, the protein product can be detected, e.g., using a protein label such as GFP. The ability of a particular sequence to direct gene products to germ plasm can be tested by linking the test sequence to a sequence encoding GFP or some other detectable protein, and visualized using microscopic techniques.

IX. Animals and Applications of the Invention

As explained above, the invention can be used to produce sterile populations of animals, and is advantageously applied to commercially farmed species, as well as invasive or pest species.

The invention can be used for animals whose germ cells are specified by maternally inherited determinants according to a "pre-formation" process. These maternal determinants are present in the germ plasm (or polar plasm), a zone found in the cytoplasm of the egg cells of evolutionary distant organisms (e.g., *Caenorhabditis elegans*, *Drosophila melanogaster*, zebrafish, and *Xenopus laevis*). Accordingly, the invention can be used, e.g., in fish, amphibian, shellfish, crustaceans, mollusks, insects, and other arthropods. As the zygote undergoes mitotic divisions the germ plasm is ultimately restricted to a few cells of the embryo. These germ cells then migrate to the gonads and eventually differentiate into functional eggs or sperm.

Fish and shellfish are a primary focus because these animals (i) can reproduce and survive in a wild environment and are prone to establish feral populations. (ii) have native relatives, raising the possibility of gene flow to or in competition with them (iii) can be genetically modified to produce lines with improved growth rates, disease resistance, or food conversion ratio. Protection of intellectual property is also important for certain aquarium or pet fish species, such as GlowFish®. This technology provides a mean to produce monosex male populations without hormonal treatment (which is undesirable for environmental reasons). All male populations are advantageous in species where males grow faster than females (e.g., tilapia).

There are economic advantages to sterile fish. Sterile fish improve culture performance. In modern fin-fish aquaculture, high growth rates cause captive fish to sexually mature earlier than wild type animals, and before the fish reach optimal marketable size. Early sexual maturation reduces growth, deteriorates flesh quality (color, taste, and texture), and increases mortality. Sterile fish never undergo sexual maturation and as a consequence, have (i) a better food conversion ratio, as energy is not lost to gonad development; (ii) increased growth rate; and (iii) a prime market condition that is maintained throughout the reproductive season.

Insects are another important application. There is a pressing need for a technology to control pest insects that can replace radiation-induced sterile males for mass releases (SIT). The drawbacks of SIT, which relies on irradiation, include (i) the need for repeated releases; (ii) time-consuming sex separation to avoid release of female insects (which often have more negative impacts on humans, livestock, and crops); (iii) ionizing radiation often affects male health, lifespan, and fitness to mate, which makes them less able to compete with wild males; (iv) the technique is species specific, and (v) high cost.

The maternally induced sterility techniques of the invention remove the need for radiation facilities; allow for inexpensive production of monosex male sterile populations; result in fit and healthy sterile males; and apply to a wide array of species.

Remarkably, a single release of sterile individuals according to the invention could be used to control pests and invasive species. Exemplary target species include mollusks (e.g., zebra mussel, *Ampullariidae*, *Bithynia tentaculata*, *Cipangopaludina chinensis*, *Corbicula fluminea*, *Dreissena polymorphs*, *Potamopyrgus antipodarum*, *Rapana venosa*), fish (e.g., *Alosa pseudoharengus*, *Channa argus*, *Cyprinus carpio*, *Gymnocephalus cernuus*, *Hypophthalmichthys molitrix*, *Hypophthalmichthys nobilis*, *Monopterus albus*, *Neogobius melanostomus*, *Oreochromis aureus*, *Petromyzon marinus*, *Pylodictis olivaris*), and insects (e.g., hemiptera (*Aphis melinus*), diptera (mosquitoes and flies such as tsetse fly, *Rhagoletis pomonella*, *Ceratitis capitata*, *Anastrepha ludens*), Lepidoptera (e.g., *Agrotis munda*, *Euxoa auxiliaris*), and coleoptera (e.g., the mountain pine beetle *Dendroctonus ponderosae*, *Xyleborus glabratus*, *Diaprepes abbreviatus*).

A readily reproducible line of sterile insects would allow for genetic engineering of beneficial species (e.g., honey bees) to improve desirable traits (disease resistance, resistance to insecticides), or to introduce mechanism to disrupt disease transmission in mosquitoes or other insect vectors. For background in these applications, see, e.g., the Braig & Yan and Spielman articles in *Genetically engineered organisms: assessing environmental and human health effects* (2002), pages 251 and 315, respectively; and Wimmer (2003) *Nat. Rev. Gen.* 4:225-32.

The invention can also be used to generate embryos devoid of endogenous PGCs to serve as hosts for the transplantation of germ cells derived from evolutionary distant species. PGCs can be easily labeled (as described herein), and isolated from living organisms (e.g., using enzymatic tissue dissection and flow cytometry). PGCs can also be transplanted into embryos where they can further differentiate into functional sperm or eggs in the recipient organism. Xenogeneic transplantation has been performed successfully and shows that transplanted PGCs develop synchronously with endogenous gamete and are functional (Ciruna et al. (2002) *Proc. Natl. Acad. Sci. USA* 99:14919-24; Takeuchi et al. (2004) *Nature* 430:629-30; Saito et al. (2008) *Biol. Reprod.* 78:159).

If the time necessary to reach sexual maturation is shorter for the host species than the donor species, or if the host species can be reared more efficiently (smaller size, easier rearing techniques), this technology can reduce the time, cost, rearing space, and labor associated with seed production for commercial aquaculture. Furthermore, xenotransplantation can be used for genetic conservation. Large-scale application of this technology requires: (i) complete germ line replacement and (ii) inexpensive and efficient production of host embryos for transplantation. Both of these requirements are met using the MSC technology described herein.

It is to be understood that the Examples and embodiments described herein are for illustrative purposes only. Those of ordinary skill will appreciate that various modifications or changes to the presently disclosured invention are to be included within the spirit and purview of this disclosure and the scope of the appended claims. All publications, patents, and patent applciations cited herein are hereby incorporated by reference in their entirety for all purposes.

X. Examples

Material and Methods

Animal Maintenance, Egg Production and Fertilization:

Zebrafish (wild type strain and transgenic lines) were maintained in recirculating culture systems and reared in conditioned water at 28.5° C. on a 14-h light/10-h dark cycle. Adult zebrafish were fed daily with flake food (TretraMin). Embryos obtained by spontaneous spawning were fed twice daily with live brine shrimp. Embryos were collected and staged as described (Kimmel et at (1995) *Dev. Dyn.* 203, 253-310). All experiments were conducted under an approved IACUC protocol. For rainbow trout (*O. mykiss*) and Atlantic Salmon (*Salmo salar*), gametes were maintained at 4° C. under oxygen for a maximum of 4 days. Every day, one to two batches of eggs were fertilized (25 ml of eggs with 1-2 ml of sperm). Sperm activation and fertilization were performed in Ringers solution to prevent hardening of the egg chorion. For each batch of injected eggs, ~100 of non-microinjected eggs were kept to control for fertilization. Injected and non-injected eggs were placed in our incubator/rearing system (recirculating water at 8-10° C. Fertilization rate/survival was assayed in batches of control eggs at ~20 days post fertilization.

Constructs: Vectors I-SceI zpc:zbax:dnd (MSCzpc) and I-Sce I kop:zbax:dnd (MSCkop):

A 1093 by NcoI-PstI fragment, containing bax:dnd 3'UTR, was digested and purified from the vector that was developed for use in our preliminary studies (Litmus 28i-bax:dnd). The purified fragment was subcloned into NcoI-PstI digested and gel purified vector backbones I-SceI zpc:egfp:dnd or kop:egfp:dnd. Ligations were transformed into 10F' competent cells (Invitrogen), plated, and transformant colonies were screened to identify the two plasmids bearing the Bax expression cassettes flanked by the I-SceI sites.

Vector Litmus 28I-eGFP:nos1:

Oligonucleotide primers were designed to amplify a 610 pb nanos 1 3'UTR (nos1): (sense: 5'-GCGAAGCTTGAT-GCTCCGGGAGATTTG-3' (SEQ ID NO:1) and antisense 5'-CCCAAGCTTAGAGAAAATGTTTATATTTTCC-3' (SEQ ID NO:2)), both of which included the restriction site HindIII at the primers end. PCR was carried out using zebrafish genomic DNA (20 ng and 600 ng). The reaction was performed for 30 cycles under the following thermal condition: 94° C. for 30 s, 56° C. for 30 s, and 72° C. for 55 s. The PCR product was cloned into PCR-TOPO2.1 plasmid vector (Invitrogen). Nanos 1 3'UTR was than subcloned between HindIII sites of Litmus 28i-eGFP:dnd to generate Litmus 28i-eGFP:nos1 (FIG. 3A2). Plasmids with nos1 in the correct orientation, (SphI restriction digest analysis) were selected for the transcription reaction.

Litmus 28i-ssbax:nos1:

Oligonucleotide primers flanking a bax *salmo salar* sequence (NCBI Accession # BT048648) were designed using Primer Select (5'-ATGGCAGACTCCCGA-GAAAGAAG-3' (SEQ ID NO:3) and 5'-TCAGCGT-GTTTTCCTCCAGTAA-3' (SEQ ID NO:4)) and used to amplify a 615 pb ssbax coding sequence. PCR was carried out using Atlantic salmon cDNA (20 ng and 600 ng) generated from muscle, pituary gland and spleen tissue. The reaction was performed for 30 cycles under the following thermal condition: 94° C. for 30 s, 60° C. for 30 s, and 72° C. for 40 s. A PCR product of the expected size was identified on agarose gel from the reaction containing spleen cDNA. The PCR product was cloned into PCR-TOP02.1 plasmid vector (Invitrogen). The ~620 pb ssbax EcoRI fragment was digested from the TOPO vector, gel purify and ligated into Limus 28i-eGFP:nos1 previously linearized with EcoRI, gel purify and alkaline phosphatase treated. The resulting new constructs (Litmus 28i-ssbax:nos1) with the insert in sense and antisense orientation were transformed into competent *E. coli* cells (Invitrogen). Cloned plasmids were screened by restriction digest (Hind III) to select appropriate expression vector.

Microinjection:

Zebrafish embryos were microinjected using established technologies with a pressure Microinjector (FemtoJet, Eppendorf, Germany). Prior to microinjection, the 2 MSC constructs were amplified, purified (Qiagen Maxiprep kit (Qiagen, USA)), and linearized with Iscel (New England Biolab). The two plasmids were microinjected with I-SceI meganuclease (DNA: 10 µg/µl; commercial meganuclease buffer (New England Buffer, USA): 0.5 ml meganuclease I-SceI: 1 units/µl; 0.1% phenol red) through the chorion into the cytoplasm of the one-cell stage embryos.

Detection of the MSCs and GFP Transgenes by qRT-PCR:

All injected zebrafish raised to ~1 month of age were anesthetized, fin clipped and placed individually in small jars while their fin DNA was extracted (R Corbett robotic system) and genotyped using quantitative real time PCR (qRT-PCR) to identify mosaic fish. Fertilized eggs from the breeding of a mosaic male with a wild type female were collected and DNA extracted from 3 batches of 7 embryos. DNA were PCR amplified under defined conditions (94° C., 30 sec; 58° C., 30 sec, 72° C., 45 sec) using primers designed to amplify the MSC specific junction between bax and dnd (bax fwd: 5'-GTTATTTTGGCACCCCCACCTG-3' (SEQ ID NO:5), dead end rev: 5'-CAATCACATTCGATCAAGC-CATAA-3' (SEQ ID NO:6). The GFP transgene was detected using GFP specific primers set Fwd: 5'-TACGGCGTGCA-GTGCCTTC-3' (SEQ ID NO:7) Rev: 5'-TGCGCTCCTG-GAGTAGC-3' (SEQ ID NO:8); DNA encoding beta-actin was used as an internal reference standard. All primer sets were designed with a commercial software package (Primer Select DNAstar), using identical parameters to generate amplicons of similar size.

In Vivo Overexpression Experiments:

Plasmids that contained eGFP:dnd, eGFP:nos1, zbax:dnd and ssbax:nos1 (z: from zebrafish, ss, *Salmo salar*) were linearized by Ncol digest, and in vitro transcription reaction performed following manufacturer's instruction (Message Machine T7 Kit (Ambion Inc., Austin, Tex.)). The synthesized capped chimeric RNAs were extracted with phenol/chloroform, precipitated with ethanol, and dissolved in RNAse free water at a final concentration of 100-300 ng/ul. Synthetic capped sense mRNA was injected into one-cell stage zebrafish embryos. For Atlantic Salmon and Rainbow trout, ~2-20 nl of the RNA solutions were microinjected into the blastodisc through the micropyle of embryos between 10 min and 4 h after fertilization. Fertilized eggs that had not been injected were placed in the egg-rearing system to control for successful fertilization/survival. To assay zebrafish bax-functionality, treated *salmo salar* embryos were coinjected with eGFP:nos1 mRNA (50 pg/embryo) and zbax:nos1 mRNA (50-150 pg/embryo). Control embryos were injected with eGFP:nos1 mRNA alone (50 pg/embryo) and zbax:nos1 mRNA alone, and wild-type (WT) embryos received no injection.

PGC Development Analysis:

PGCs were first analyzed in embryos at the prim-5 stage (~24 hpf), when greater than 95% of PGCs have migrated into the genital ridge region. Live embryos were visualized with fluorescence microscopy, and PGC development was analyzed by counting the number of PGCs on either side of the genital ridges, and the number of ectopic PGCs. For acridine orange (AO) staining, live embryos were manually dechorionated at 24 hpf and placed in AO at 16.7 #g/ml in embryo medium for 20 min. The embryos were anesthetized in 0.0003% 3-amino-benzoic acid and placed under fluorescent microscopy for analysis.

Histology:

For histology, tissue was fixed overnight in Bouin's fix (Sigma), dehydrated, and infiltrated in paraffin. Paraffin sections were cut at 0.5 µm and stained with Hematoxylin and Eosin (Pacific Histology, San Diego, Calif.).

qRT-PCR and RT-PCR:

Gonads were isolated from sterile, partially fertile, and wild-type male and female zebrafish at 2-3 month of age. Tissue was collected in Trizol Reagent (Sigma) and RNA extracted following manufacturer's instruction. MNLV reverse transcriptase was used for first strand cDNA synthesis. Control reactions with no reverse transcriptase were performed in parallel. RNA prepared for qRT-PCR was treated with DNAse I. The following primers were used for RT-PCR reaction (uppercase) and qRT-PCR (lowercase): vasa fwd: 5'-TGGACTATATTTTCCTTGCTGTTG-3' (SEQ ID NO:9) and 5'-cgtgagtggcagcaatect-3' (SEQ ID NO:10); zbvasa rev 5'-TATTCCCATTCCTCATCGTCTGC-3' (SEQ ID NO:11) and 5'-gtgtaggcttcacatatccag-3' (SEQ ID NO:12); zb sox9a fwd: 5'-CACCCTACGCTGGAGGATACG-3' (SEQ ID NO:13) and 5'cggtgaagaacggccagagc-3' (SEQ ID NO:14); zb sox9a rev 5'-CCATCATGCACTGAACGAACA-3' (SEQ ID NO:15) and 5'-ctgtagagtcagcaatgggt-3' (SEQ ID NO:16); β-actin fwd: 5'-GACATCAAGGAGAAGCTGTGC-3' (SEQ ID NO:17) β-actin rev: 5'-GAGGGCAAAGTGGTAAAC-3' (SEQ ID NO:18); and cyp19a1a fwd 5'-CTGCTAGCCATCAGACACCA-3' (SEQ ID NO:19); cyp19a1a rev: 5'-ATCCTGCAACTCCTGAGCAT-3' (SEQ ID NO:20).

Data Analysis:

Total PGC numbers represent the sum of genital ridge and ectopic PGCs. Mean total PGCs and mean ectopic PGCs were statistically compared using an unpaired t test, significance set at P<0.05.

Example 1: Proof of Principal Using Zebrafish

Figure 5:
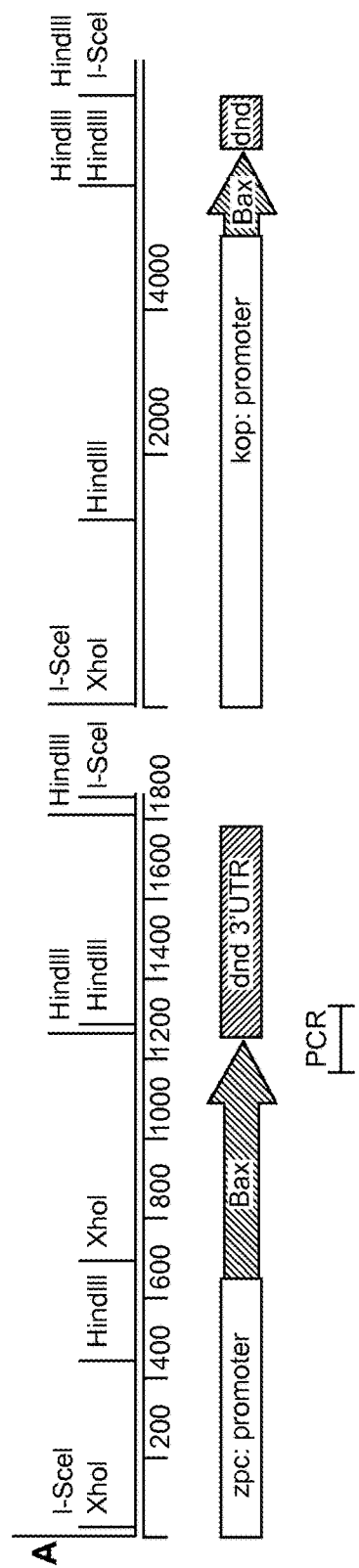
FIG. 5: (A) Schematic representation of MSCzpc and MSCkop constructs. PCR at the junction between bax and dnd was used to identify transgenic fish by qRT-PCR. (B) Representation of transgenic MSC lineages established from different F0 male founders (bold). Vertical bars represent the genotype of F1 progeny positive for the MSC transgene alone (black) or both MSC and GFP transgenes (green and back double bar). The phenotypic sex and number of F1 progeny are indicated as follow: males (m1, m2, m3 . . . ) and females (f1, f2, f3 . . . ). Percentage of F2 male progeny and total number of F2 offspring (n) from different F1 lines are indicated. The progeny of F1 females circled in the figure were selected to study the effect of the maternally inherited transgene on PGCs (expressing GFP). (C1) PGCs in an embryo from F1 female MSCzpc3 showing characteristic of cells undergoing apoptosis with membrane blebbing (diffuse GFP on the edges of the cell) and formation of apoptotic bodies (shown by arrows). (C2) Fluorescent microscopy of acridine orange-treated embryo derived from F1 female MSCzpc11 (f1). (D) Fluorescent images of 24 hpf and 48 hpf embryos from F1 female (f2) MSCzpc3 showing variable defect in PGCs. Embryos in group A displayed normal PGC count, while group B showed reduced number of PGC and Group C had no visible PGCs at 48 hpf. (E) Mean number of GFP labeled PGCs in the progeny of different MSC lines. Embryos derived from MSC females (left) show significant reduction of PGCs (up to 90%), while embryos derived from an MSC male (right) display normal PGC numbers. Approximately 20 embryos were used to calculate the average number of PGCs for each transgenic line tested. Vertical bars represent standard deviation.

To evaluate the functionality of the Maternal Sterility Construct (MSC) and document ablation of PGCs in a model organism, we created transgenic zebrafish that produce bax-dnd 3'UTR RNA under the control of either a zona pellucida or askopos oocyte-specific promoter (FIG. 5A). If the maternally contributed bax-dnd 3'UTR RNA is expressed during oogenesis and remains present in the eggs, the embryonic development will result in individuals that lack germ cells. The result will be a sterile generation, or what can be called a grandchildless phenotype.

To ablate PGCs, we relied on the activation of the intrinsic apoptotic machinery by ectopic over-expression of the zebrafish pro-apoptotic gene bax. Bax belongs to a family of key protein regulators of apoptosis (Bcl-2 family (van Delft & Huang (2006) *Cell Res.* 16:203-13)) that contain both anti-apoptotic (e.g., Bcl-2 and Bcl-XL) and pro-apoptotic (e.g., Bax, Bik, Bad) members. The ratio of these molecules is a critical determinant of cell fate. Elevated anti-apoptotic gene expression favors extended survival of cells, while increasing levels of proapoptotic gene expression accelerates cell death. Precise control of cell death to remove abnormal, misplaced or excess PGCs is essential to maintain the continuity and integrity of the germline, preventing germ cells from colonizing locations other than the gonads. Bax has been shown to be involved in germ cell apoptosis within the male and female gonad in rat and mouse (Knudson et al. (1995) *Science* 270:96; Perez et al. (1999) *Nature Gen.* 21:200-03; Yamamoto et al. (2000) *Soc. Study Reprod.* 63:1683-90; De Felini et al. (1999) *Cell Death and Diff.* 6:908-15). Bax and other pro-apoptotic genes have also been shown to be involved in death of PGCs that are misdirected during migration from the site of origin toward the gonad in zebrafish, trout and mouse embryo (Stallock et al. (2003) *Development* 130:6589-97). However, ablation of PGCs by ectopic expression of Bax, or any other protein delivered transgenically, has not been reported.

To initially demonstrate the feasibility of our approach, we generated a plasmid with zebrafish bax-1 fused to the 3'UTR of the zebrafish dnd gene, under the control of a T7 promoter (FIG. 4A). We prepared a capped synthetic bax-dnd 3'UTR mRNA from this construct in vitro (FIG. 4B) and injected various concentrations (80 pg to 2 ng) into 1-2 cell stage zebrafish embryos from a transgenic female expressing GFP from the promoter zpc and with a dnd-3'UTR (as shown in FIG. 2, this transgenic line produces GFP labeled PGCs).

Figure 4:
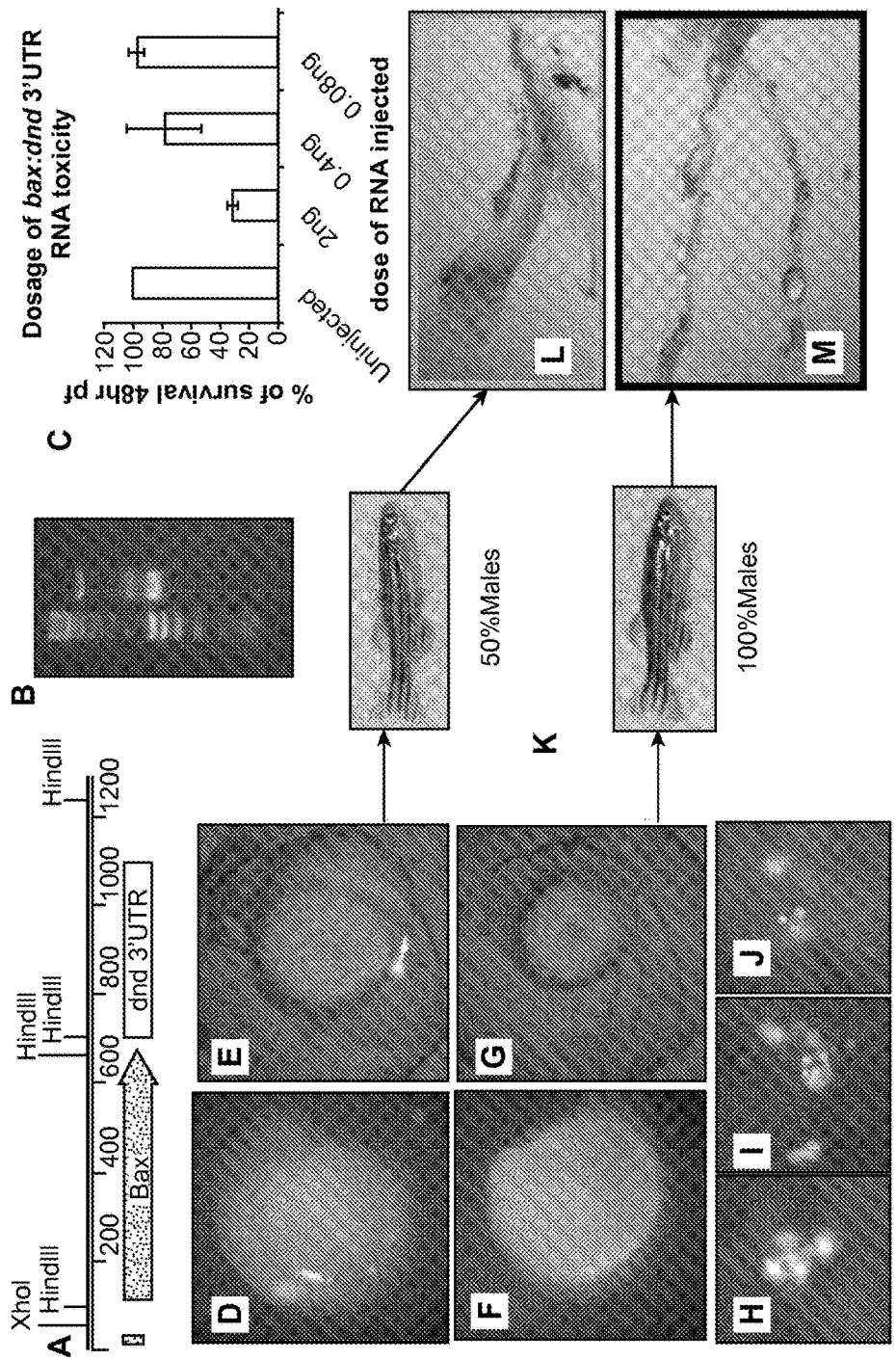
FIG. 4: Bax-mediated ablation of PGCs. (A) Depiction of Litmus 28i bax:dnd 3'UTR construct used for expression of synthetic capped bax:dnd mRNA. (B) Bax:dnd mRNA from (A) as visualized on agarose gel. (C) Pro-apoptotic zebrafish Bax induces death in a dose-dependent manner. (D-G) Fluorescent images of 24-hpf (D&F) and 48-hpf embryos (E&G). (D&E) show mock-injected embryos (control group). (F&G) show embryos injected with synthetic bax: dnd 3'UTR mRNA (test group). (H-J) Time-lapse frame of a cluster of PGCs during early somitogenesis in test group embryos. Note the diffuse GFP on the edges of the cells suggesting membrane blebbing (H) and subsequent fractionation into small cell fragments (I, J) characteristic of apoptotic bodies. (K) Sex ratio based on the analysis of 20 embryos in the control and test groups. (L) Dissected gonads from 3 month old control injected embryos. (M) Dissected gonads from bax:dnd 3'UTR RNA injected embryos.

Groups of 15-20 embryos were used for each mRNA dose. At the lowest concentrations, no specific difference in survival was observed between mRNA injected groups and the non-injected control. Higher concentrations triggered dose-dependent embryonic mortality (FIG. 4C), characterized by disintegration of the blastomeres and yolk soon after midblastula transition. This suggests that high doses of Bax-1 induce apoptosis in embryos. Reducing the amount of bax-dnd-3'UTR mRNA injected results in decreased mortality. Embryos injected with 400 pg of RNA that survived gastrulation and appeared phenotypically normal were analyzed under fluorescent microscopy (FIGS. 4 F&G) and compared to PBS injected sibling embryos (FIGS. 4 D&E).

The results demonstrated that PGCs in bax-dnd 3'UTR RNA injected embryos were dying: (i) fluorescent PGCs in RNA treated embryos were dramatically reduced in number or completely absent in 48 hpf (hours post fertilization) embryos and (ii) PGCs in RNA injected embryos at 18-24 hours post fertilization exhibited morphological changes which included membrane blebbing, followed by formation of apoptotic bodies characteristic of cells undergoing programmed cell death (FIG. 4 H, I, J) (Rich et al. (1999) *Nat. Cell. Biol.* 1:E60-71). These embryos showed no somatic defects as they continued to develop. We raised 20 RNA injected embryos to adulthood and found that all developed into phenotypic males (FIG. 4K) that displayed normal male sexual behavior (induced spawning when paired with wild type females). Control PBS-injected siblings produced both male and female progeny with a ~50% sex ratio (FIG. 4K). In addition, 12 of the 20 bax-treated fish were completely sterile as judged by their inability to fertilize eggs in three consecutive matings. To confirm the sterile phenotype, we dissected the gonad of sterile males and found a translucid tube-like structure (FIG. 4M) in place of the ovoid opaque structure found in fertile male (FIG. 4L).

Example 2: Germ Line Transmissible Transgenic Zebrafish

We next created transgenic zebrafish carrying our two maternal sterile constructs, zpc:zbax:dnd (MSCzpc) and kop:zbax:dnd (MSCkop) (FIG. 5A). The vectors were injected into two batches of 200 fertilized eggs. A 60-70% survival rate was recorded three days after microinjection. At one month of age the surviving embryos (~50%) were fin clipped to detect individuals carrying the transgene. Out of 66 and 80 fish screened, 25 (37%) and 34 (42%) were tested positive for the MSCkop and MSCzpc transgenes, respectively. The remaining PCR positive fish were raised to sexual maturity, sexed, and identified males were crossed with wild-type female broodstock to determine their ability to transmit the construct to their progeny. Of the 11 and 13 males screened for MSCkop and MSCzpc respectively, 2 and 4 produced at least one clutch of PCR positive embryos (3 clutches of 7 embryos were screened for each parental pair).

These 6 male founders capable of germline transmission were crossed with heterozygous females carrying either zpc:eGFP:dnd (GFPzpc) or kop:eGFP:dnd (GFPkop) constructs. The same GFP lines were used in all subsequent crosses to establish a marker for germ cell evaluations. Progeny (~10-50 embryos/founder/construct) from these crosses were raised to ~1 month of age, and screened by PCR to identify the fish carrying the MSC and GFP transgenes. In average 3 out of 10 embryos tested positive for the MSC(s) (33.5%+/−9%) indicating a relatively low degree of MSC germ line mosaicism. These F1 fish were raised to maturity and sexed. Overall, we identified 19 F1 males and 20 F1 females positive for the MSCs (FIG. 5B). The equal sex ratio observed in F1 progeny derived from transgenic male founders suggest there was no paternal or zygotic effect of the transgene on sex determination. We used F1 males and females from each line to produce the next generation of MSC transgenic fish.

Example 3: Confirmation of PGC Ablation in F2 Developing Embryos

A maximum of 3 F1 males and 3 F1 females per line were used to establish lineages. F2 embryos derived from females carrying both GFP and MSC transgenes were analyzed by fluorescent microscopy and PGC numbers (i.e. GFP positive cells) were recorded at 24 and 48 hours post fertilization (hpf). If the transgenes are indeed under specific maternal expression, we expect F1 MSC females to produce embryos with reduced or absent PGCs, relative to control embryos (i.e. those produced by female GFP broodstock). More than 90% and 70% respectively of all embryos from F1 females of MSCzpc22 and MSCzpc9 lines completely lacked visible GFP+ cells. In contrast, F1 females from lines MSCzpc11 and MSCzpc3 produced only 5-10% of embryos with no detectable GFP+ cells. The three F1 Females of line MSCkop2 also produced 30-80% of embryos with no GFP+ pattern. Furthermore, all other embryos produced by GFP MSC females had PGCs number ranging from normal to markedly reduced. The mean numbers of PGCs per embryo (n=20) collected from each F1 female are shown in FIG. 5E.

F2 embryos produced by GFP broodstock females crossed with F1 MSC or wild-type males had approximately 30 PGCs (FIG. 5E), a normal count (Yoon et al. (1997) *Development* 124:3157), suggesting no paternal or zygotic effect of the MSC transgene on PGCs survival.

Analysis of Earliest Defect in PGCs.

To determine more precisely the stage at which PGCs become defective, we monitored embryos derived from female MSCzpc3, which produced embryos with PGC counts at 24 and 48 hpf ranging from normal to zero (Group A, B and C respectively (FIG. 5D)). At 30% epiboly (thinning and spreading of cell layers during gastrulation, ~5 hpf) we found GFP-cells in all embryos (FIG. 5C1). At ~10 hpf, groups of embryo with reduced PGC numbers could clearly be identified.

PGC Death by Apoptosis.

In embryos where GFP+ cells eventually disappeared, we detected PGCs with morphological signs of apoptosis such as membrane blebbing followed by formation of apoptotic bodies. Embryos derived from MSC F1 female lacking the GFP construct (FIG. 5C2 line MSCzpc11) were stained with the vital dye acridine orange (AO, acridinium chloride hemi-(zinc chloride)) and analyzed under fluorescent microscopy. As shown in FIG. 5C2, green fluorescent cells appeared as a cluster in the gonadal anlagen. This observation suggests that sterility is due to early apoptosis of Primordial Germ Cells. Further confirmation that the maternal effect-sterile phenotype is due to bax-induced apoptosis was shown in rescue experiments, as described below.

In zebrafish, overexpression of Bcl-XL blocks apoptosis induced by a minimum lethal dose of Bax (Kratz et al. (2006) *Cell Death & Differentiation* 13:1631-1640). We produced synthetic capped Bcl-XL:dnd 3'UTR mRNA and microinjected a titration of this transcript in one-cell stage embryos derived from MSC-females. Out of 10 embryos that survived the injection, 8 became males while 2 became females. All 10 were fertile. Non-injected control siblings (n=20) were all male and 90% of them were sterile. To test if the absence of GFP expression at 48 hpf is a reliable indicator of sterility, we sorted GFP-positive and negative embryos in lines MSCzpc3 and MSCkop2 and raised them separately to sexual maturation (~3-4 months of age). We further separated embryos from line MSCzpc3 in groups of 0-2; 3-6; and 7-13 PGCs (FIG. 5D). We found a clear correlation with sterility in an adult and number of PGCs observed in an embryo.

Example 4: Demonstration of Maternally Directed Functional Sterility in Adults

MSC Transgenic Females Preferentially Produce Male Offspring.

Fish embryos (zebrafish and medaka) with reduced or absent germ cells prior to sexual differentiation develop as male (Houwing et al. (2007) *Cell* 129:69-82; Slanchev et al. (2005) *Proc. Natl. Acad. Sci. USA* 102:4074-79; Kurokawa et al. (2007) *Proc. Natl. Acad. Sci.* 104:16958-63). Here, males were identified visually based on body shape, coloration and absence of urogenital papillae. In all of our lines, we observed a strong bias toward male development. Although the male bias varied between lines, the number of males was consistently in excess of 70% in the progeny of at least 6 different MSC F1 females cross with wild type male (FIG. 5B). Interestingly, the MSC F1 female producing embryos with the strongest PGC defect (>85% reduction in PGC count in embryos from lines MSCzpc9, zpc22, FIG. 5E) also produced the strongest male bias (90-100% male) (FIG. 5B). Progeny masculinization was not observed from crosses between F1 MSC-males and wild-type females (males with MSC paternal inheritance produce 50% male 50% female progeny) and progeny were fertile (FIG. 5B). The varying level of penetrance of the grandchildless phenotype can be due to differences in integration sites, copy number of the transgene in the genome, or epigenetic processes which ultimately affected transgene expression levels among the different lines.

We sexed the progeny of MSCzpc3 previously sorted for PGC counts. Embryos that had less than 3 PGCs (n=12) all developed as males. Between 3 and 6 PGCs resulted in 70% of the embryos developing as males (n=10). Embryos that had between 7 and 13 PGCs developed with a normal sex ratio despite the severe reduction in PGC counts. Thus, a reduction of more than 90% of the PGCs at 48 hpf will generate an all-male zebrafish population.

MSC Transgenic Females Produce Sterile Progeny (Grandchildless Phenotype).

Figure 7:
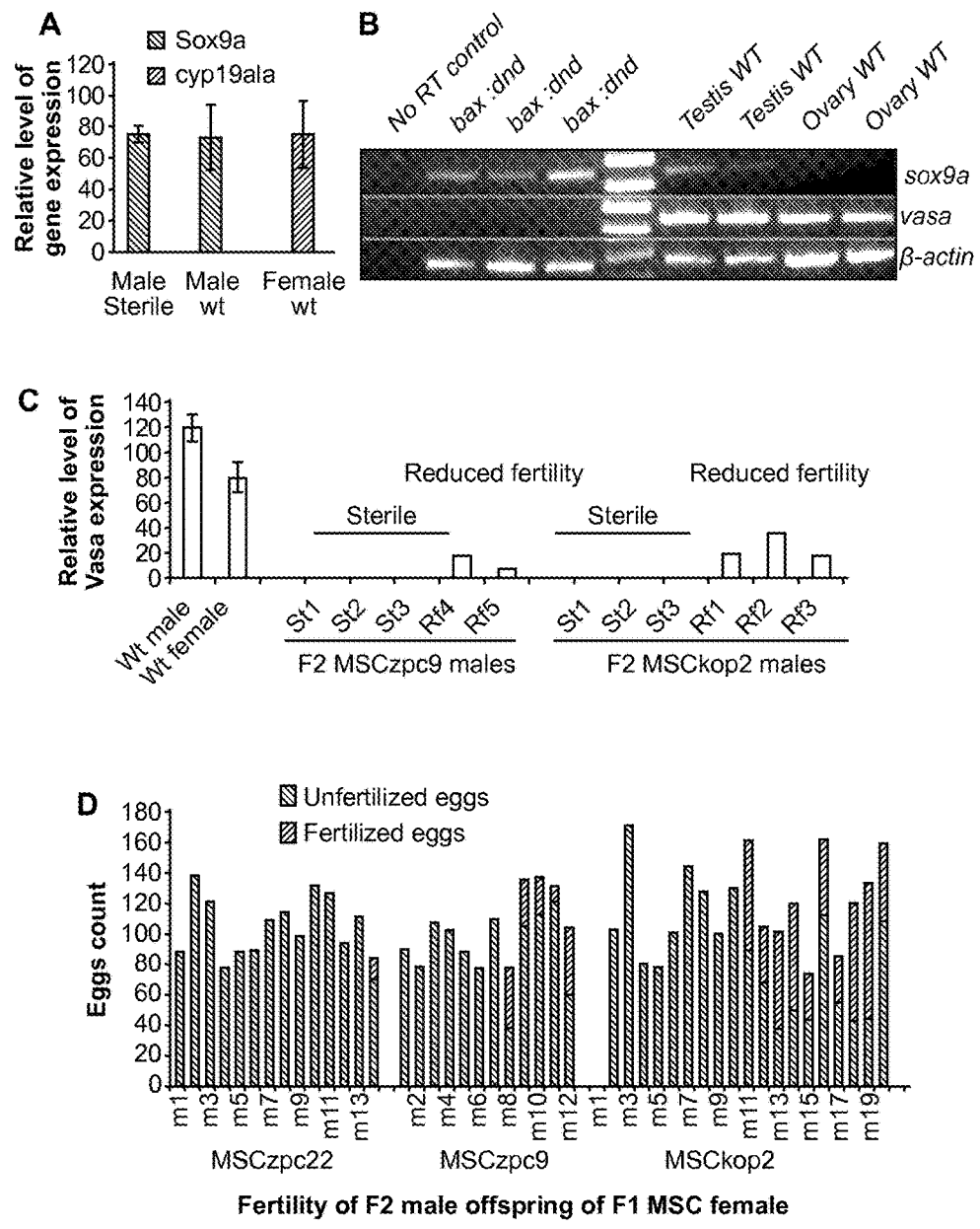
FIG. 7: Evaluation of sterility phenotype: (A) Adult germ cell-depleted gonads (dissected from F2 sterile fish in line MSCzpc22) exhibited expression of the male specific marker sox 9a at levels similar to wild-type testes. In contrast, we did not detect expression of the ovarian follicle marker cyp19a1a. Each experiment was performed in triplicate. (B&C) Adult germ line deficient gonads show no expression of the germ cell specific marker vasa. (B) RT-PCR analysis of sox9a and vasa genes from gonadal tissue dissected from 4 wild-type (2 males and 2 females) and 3 sterile fish. Negative controls lacking reverse transcriptase (no RT) are shown in lane 1. (C) Q-RT-PCR analysis was performed on dissected gonads from 6 sterile males, 5 males with reduced fertility and wild-type male and female control. We used the house-keeping gene β-actin, to normalize RNA level between samples. No expression of vasa was detected in samples from sterile fish. The relative level of vasa expression in gonad from fish with reduced fertility rates was 60-90% lower than wild-type male and female. (D) Fertilization rate from progeny of F1 MSCzpc9, MSCzpc22 and MSCkop2 females. Bars (upper portion, where present) indicate number of fertilized eggs and blue bars show non-fertilized eggs.

To determine whether the reduction in number and/or complete ablation of PGCs results in reduced fertilization rates and/or sterile fish, we tested F2 males progeny from three lines (MSCzpc9, MSCzpc22 and MSCkop2). These males all successfully induced wild-type females to lay eggs. The sum of all fertilized and unfertilized eggs was recorded after 2-3 consecutive matings (FIG. 7D). We found that these 3 lines displayed varying penetrance of a "grandchildless" phenotype. Only one of the 14 F2 males in line MSCzpc22 produced viable progeny. This male had a low fertilization rate of ~15%. In line MSCzpc9, only 33% (4/12) of the males produced viable progeny. Their fertilization rates ranged between 20 and 80%. Finally, all GFP negative embryos (those with no visible PGCs) in line MSCkop2 developed as sterile individuals while all (10/10) GFP positive embryos became fertile adults. Sorted GFP positive embryos with as little as 1-3 visible PGCs became fertile indicating that a small number of surviving germ cells can succeed in repopulating the gonad. We found no fertility deficiency in the progeny of MSC transgenic males crossed with broodstock GFP females.

Maternal Expression of the Transgene is Necessary and Sufficient for Sterility.

Our preliminary studies with GFP broodstock lines indicated oocyte specific expression with no zygotic expression of the transgene (no GFP detected in embryos from GFPzpc or GFPkop male cross with wild type female). As such, from MSC F1 female, we should expect similar distribution of the transgene between the fertile and sterile sibling F2 fish. By qRT-PCR we found ~65% and ~68% of MSC positive respectively in GFP negative (n=36 likely sterile) and GFP positive (n=34 likely fertile) embryos from line MSCkop2. This suggests a Mendelian inheritance of two copies of the transgene (75%) in both groups. We confirmed the existence of non-transgenic sterile adult in line MSCzpc22, where 4 out of 12 F2 sterile fish lack the transgene. These results further confirm that maternal inheritance is sufficient for sterility. Thus, maternal inheritance of the MSC transgene results in both transgenic and non-transgenic sterile progeny.

Gonad Structure in Sterile Zebrafish.

Figure 6:
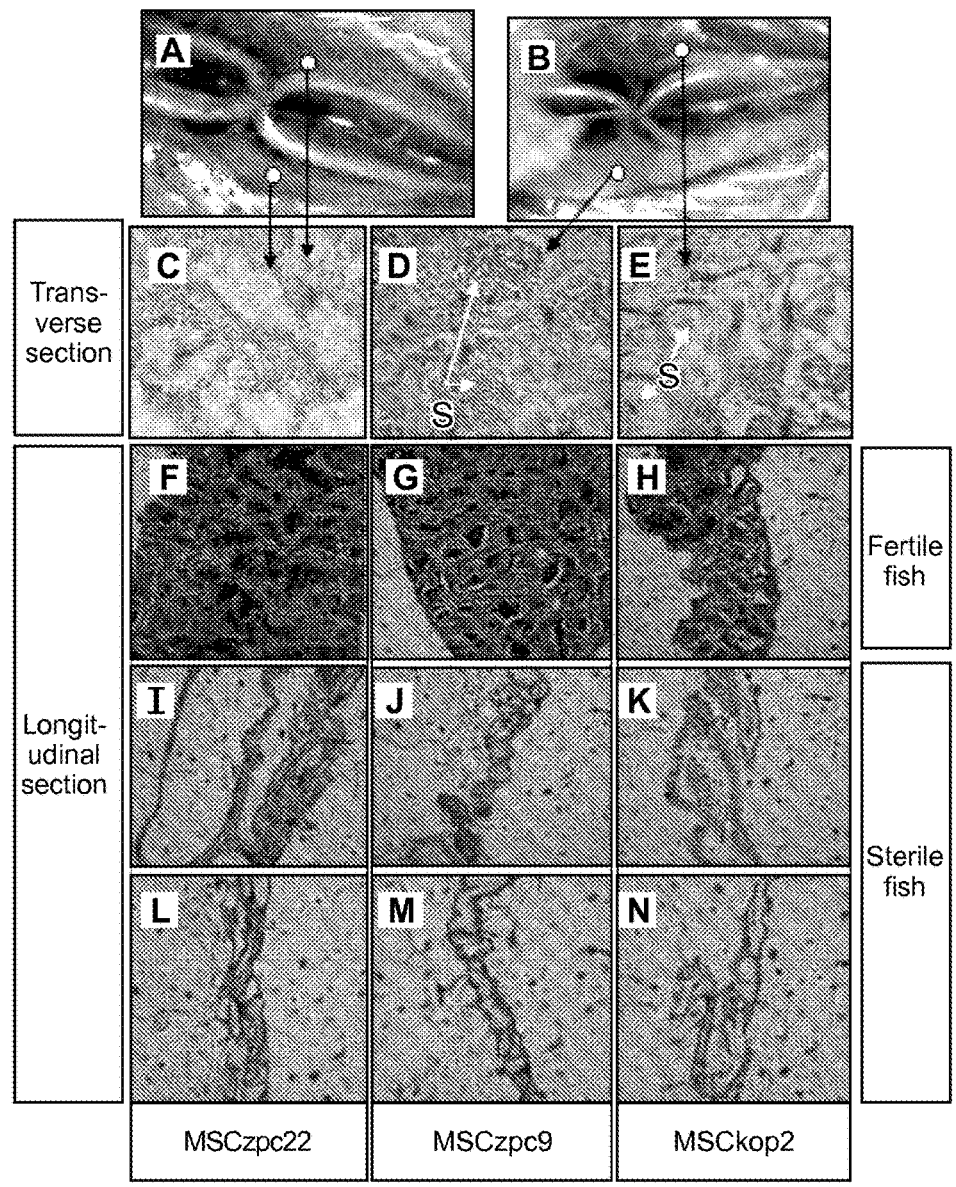
FIG. 6: External appearance of gonad in male fish. (A) Sterile (MSCzpc22) fish and (B) low fertilization rate fish from the group MSCzp3 with 0-3 PGCs showing a normal gonad on only one side rather than the normal pair. (C-N) Histology section of the gonads stained with hematoxylin and eosin (H&E). Transverse section of (C) sterile (D) wild type, and (E) atrophic gonads. The tissue is organized in tubules surrounded by basement membrane. Within the tubules, spermatozoa (S) can be seen at high density in the wild-type fish and at lower density in partially fertile fish, while no spermatozoa can be detected in the lobule lumen from sterile individuals. Sertoli cells are found within the tubules and Leydig cells are in the interstitial spaces. (F-N) Longitudinal section of aged matched F2 sterile and fertile progeny from F1 MSCzpc9 male (F) and sibling female (I, L), F1 MSCzpc22 male (G) and sibling female (J, M) and F1 MSCkop2 male (H) and sibling female (K, N).

To confirm sterility at the cellular and molecular level we evaluated the overall morphology and cellular structure of the gonad in F2 sterile fish and fertile control aged-matched individuals. Control fish had normally shaped and paired gonads. In contrast, sterile fish had a pair of translucid tube-like structures on each side of the peritoneal cavity (FIG. 6A). This observation is consistent with the results of our mRNA bax-dnd 3'UTR injection experiment (FIG. 4M). Histological sections stained with Hematoxylin and Eosin revealed that the gonads of sterile fish had organized tubules resembling testes composed of cells resembling testes-specific Sertoli and Leydig cells. These tube-like testes completely lacked germ cells (FIG. 6C).

Gonad Development in, Embryos with Reduced PGC Number.

Fish selected from the group with 1-3 PGCs, which showed reduced fertilization rate had either identical pair of smaller but normally shaped gonad or had dimorphic gonad with one small size on one side of the abdomen and a second gonad resembling that observed in sterile individuals. The reduced size gonad contained very few spermatozoa in the lobule lumen, when compared to wild type male gonads (FIG. 6E).

Gonads without Germ Cells are Testis.

To confirm that the dissected tube like structure in sterile fish is a male gonad, we measured by quantitative real time PCR (qRT-PCR) the level of expression of sox9a (Chiang et al. (2001) *Dev. Biol.* 231:149-163), a specific gene marker for Sertoli cells. Sox9a was expressed in gonads from sterile fish at a similar level to wild-type testes, indicating that Sertoli cells are present (FIG. 7A, blue bars). To further confirm that no female tissue was present, we assayed for cyp19a 1a, which is expressed in the ovaries but not in testes (Kishida & Gallard (2001) *Endocrinology* 142: 740). As with testes from wild-type males, we did not detect expression of cyp19a 1a (FIG. 7A). To further evaluate the effect of the transgene on PGCs at the molecular level, we compared expression levels of a germ cell specific gene marker (vasa) in dissected gonad from sterile partially fertile and wild-type (fully fertile) zebrafish. Expression of vasa was not detectable by qRT-PCR in sterile fish. We observed high expression in wild type fish, and an intermediate expression level in fish with reduced fertility (FIG. 7C). These results confirm histological observation that the germ line is absent in sterile fish. PCR analysis of sox9a, vasa and β-actin gene expression in dissected gonad from three sterile and four wild type fish (two males and two females) further indicates that the dissected tissue in sterile fish contains testes-specific somatic cells (sox 9a positive), but no germ cells (vasa negative) (FIG. 7B).

Example 5: The Sterility Phenotype is Associated with the Level of MSC Transgene Expression and can be Propagated We found that the severity of the maternally induced phenotype (% males and sterile progeny) correlates well with the level of maternal bax-dnd 3'UTR mRNA (as measured by qRT-PCR) in the fertilized eggs (Table 1). The MSC-line with the most severe male bias/sterile phenotype (e.g. MSCzpc22) expressed the highest levels of bax-dnd 3'UTR mRNA. A transgenic line with weak male bias (e.g. MSCzpc3) and mostly fertile offspring expressed very low levels of the MSC transgene. Lines with intermediary phenotypes had intermediate level of transgene expression. This correlation is extremely useful as an indicator of the strength of the maternal phenotype and can be used to select for the most penetrant grandchildless MSC-lines in early screen.

TABLE 1

Correlation between the level of MSC mRNA in embryos (F2, F3) produced from two subsequent generation of MSC- females (F1 and F2), and the percentage of a) male offspring and b) sterile progeny. The percentage of male and sterile progeny is derived from the examination of n (given number) adults for each line. The levels of bax:dnd 3'UTR mRNA in early embryos were determined by q-PCR from an average of 4 clutches of eggs for at least two females for each line. Levels of expression were normalized to the housekeeping gene β-actin and expressed as a percentage of the highest level of expression measured in line MSCzpc22.

| Lines | % Male offspring (from MSC- female) | | % Sterile progeny (from MSC-female) | | Relative levels of MSC mRNA expression in the eggs (Sdv) | |
|---|---|---|---|---|---|---|
| F1 or F2 females | F2 generation | F3*** | F2 generation | F3*** | F2*** | F3*** |
| MSCzpc22 | 100% (n = 40) | 100% (n = 18) | 92% (n = 14) | 94% (n = 17) | 100% (21%) | 100% (16%) |
| MSCzpc9 | 91% (n = 22) | 100% (n = 30) | 60% (n = 12) | 71% (n = 7) | 19% (8%) | 18% (5%) |
| MSCkop2 | 71%-100% | nd | 52% (n-10) | 25% (n = 8) | 14% (2.5%) | 12% (2%) |
| MSzpc3 | 70% (n = 27) | nd | 5% (n = 20) | nd | 2% (02%) | 1% (0 2%) |

SD: Standard deviation.

The Sterility Phenotype can be Propagated.

Transgenic lines propagated through the male lineage maintained a robust sterility phenotype over at least 2 generations. We found very similar levels of MSC mRNA in embryos produced by F1 and F2 females (Table 1, F2 and F3 embryos) suggesting that the sterility phenotype is maintained between subsequent generations. Indeed, with few exceptions we confirmed that F1 and F2 MSC females (produced from F0 and F1 males of the same line) produce offspring displaying a similar male bias and comparable sterility phenotype. The rare cases where we observed reduced levels of MSC mRNA in subsequent generations and decreased strength of the phenotype were likely due to decreased copy numbers of MSC transgenes associated with Mendelian inheritance of multiple integrants of the transgene. Accordingly, we found similar male and sterility phenotype in the F2 and F3 progeny from F1 and F2 MSC-females.

Example 6: Application in Other Finfish

Targeted PGCs Expression in Salmonids.

Zebrafish and Salmonidae belong to different fish clades (ostariophyans and euteleost respectively) where the germ plasm RNA localization machinery may have evolved differently. We sought to determine if the 3'UTR of the zebrafish dead end (dnd) and nanos1 (nos1) can target RNA translation to the germ cells in the salmonoids Atlantic salmon (*Salmo salar*) and rainbow trout (*Oncorhynchus mykiss*). Zebrafish nanos1 (nos1) 3'UTR was used in this study since its role for RNA localization appears to be conserved among teleost species belonging to all main clades of the fish phylogenetic tree (pearl danio, goldfish, loach, herring, medaka and ice goby) (Saito et al. (2006) *Dev. Biol.* 50:691). To this end, we generated high-yield transcription vector driving eGFP fused to the 3'UTR of the dnd and nos1 genes (FIG. 8A1-2).

We prepared capped synthetic eGFP:dnd and eGFP:nos1 mRNA from these constructs in vitro and injected various concentrations into 1 cell stage zebrafish (control), embryos and fertilized rainbow trout and Atlantic salmon eggs (between 10 min and 3 hpf). Following microinjection, ubiquitous GFP expression was observed in all blastomeres in zebrafish embryos (FIG. 8Z3) but expression rapidly faded in somatic cells (FIG. 8Z1). Strong GFP appeared in the PGCs soon after their specification (FIG. 8Z1). GFP labeled PGCs were clearly visible in 2 days old zebrafish embryos (FIG. 8Z4).

Figure 8:
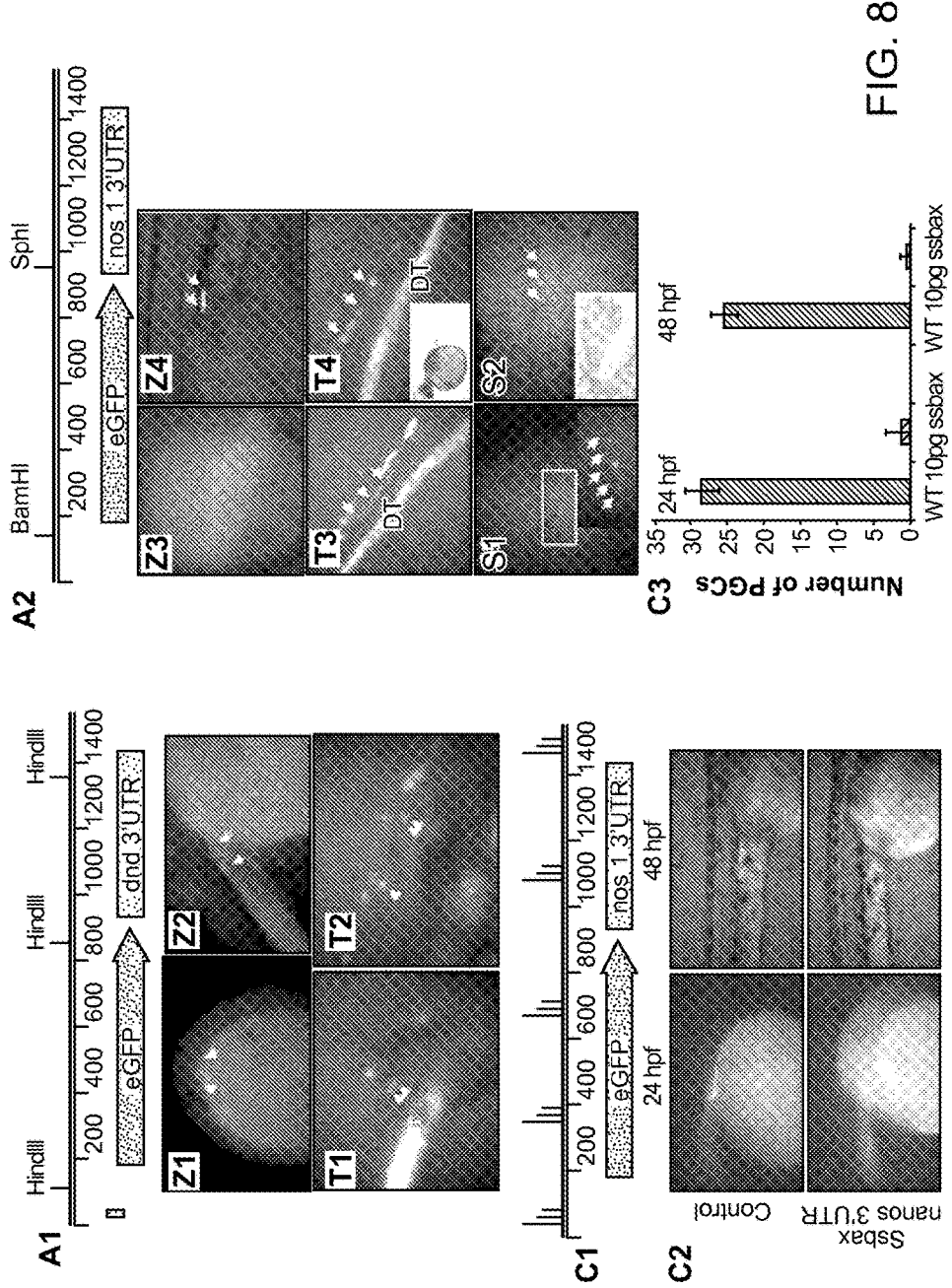
FIG. 8: (A1 & A2) GFP reporter gene construct fused to zebrafish dnd 3'UTR and nanos 3'UTR. (Z1-4) Fluorescent images of zebrafish embryos injected with 60 pg of synthetic capped RNA eGFP:dnd (Z1:20hpf-Z2:24hpf) and eGFP: nos1 3'UTR (Z3: 4hpf, Z4: 48hpf). (T1-4) 30 days old trout embryos injected at the time of fertilization with 200 pg of synthetic capped RNA eGFP:dnd (T1, T2) and eGFP:nos1 (T3, T4). (S1, S2) 20 day old Salmon embryos** injected with 200 pg of capped RNA eGFP:nos1. Arrows indicate GFP-PGCs in dorsal position relative to the digestive tract (DT) showing auto-fluorescence. Lateral view of the 30 day old eyed-stage trout* and 20 day old deyolked salmon embryos** are shown. As embryonic development proceeded, somatic cells showed declining fluorescence while continuing and intensifying GFP is observed PGCs. (C1) Schematic representation of the expression vector driving *Salmo salar bax* fused to zebrafish nos1 3'UTR. (C2) Fluorescent images of zebrafish embryos from GFP broodstock female control (mock injected) or injected with ~10 pg of synthetic capped RNA ssbax:nos1 at 24 hpf and 48 hpf. (C3) Mean number of PGCs in control (right) and ssbax:nos1 (left) injected zebrafish embryos at 24 and 48 hpf (n=8). Vertical bars represent the standard deviation.

We examined GFP expression patterns in 20 days old salmon embryos (FIG. 8S1) injected with eGFP:nos1 (FIGS. 8S1-2) and 30 days old trout embryos (FIG. 8T3) treated with either eGFP:nos1 (FIGS. 8T3-4) or eGFP:dnd mRNA (FIGS. 8T1-2). We found that ~30% of all embryos examined displayed bright fluorescent round shaped cells, located in two lines between the digestive tract and the dorsal side of the peritoneal cavity (FIGS. 8S&T). This GFP expression pattern is similar to that observed in rainbow trout embryos receiving eGFP: vasa RNA (Yoshizaki et al. (2005) *Biologly of reproduction* 73:88). This result confirms that zebrafish dnd and nos1 3'UTR can deliver mRNA and subsequently heterologous protein expression to the PGCs of Trout and Salmon. The evolutionarily conserved nature of the machinery responsible for maternal germ cell mRNA translation within PGCs makes the use of germ cell 3'UTRs particularly attractive for the delivery of specific heterologous mRNA to PGCs for a broad range of target species.

Ablation of PGCs.

To further demonstrate that the transgene can function in distant species, we tested if ectopic over-expression of bax from zebrafish and/or *Salmo salar* can ablate PGCs in *Salmo salar* and/or zebrafish respectively. We PCR amplified and subcloned a new *Salmo salar* cDNA (ssbax), whose nucleotide and translated amino acid sequences were 94% and 99% identical to the apoptotic regulator Bax published online (*Salmo salar*, Leong et al. cGRASP). We fused ssbax to zebrafish nanos1 3'UTR and placed this cassette in a transcription vector. From this construct (FIG. 8C1), we produced synthetic capped RNA ssbax:nos1 and injected various concentrations into one cell stage zebrafish embryos. We microinjected embryos from female GFP broodstock to compare the GFP expression pattern in treated and untreated embryos.

Figure 3:
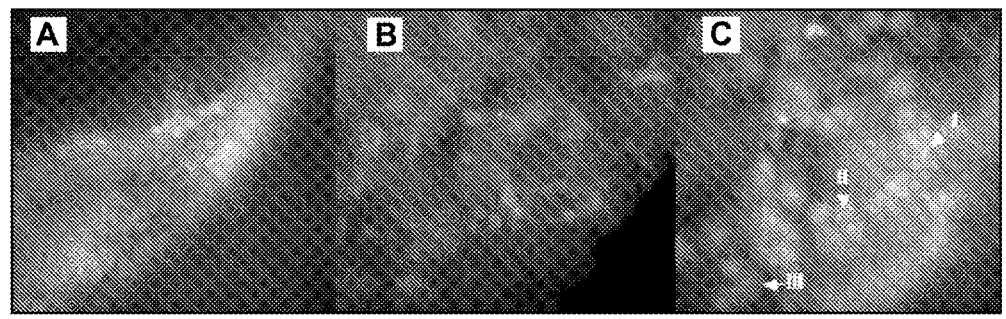
FIG. 3: Fluorescent microscopy images of transgenic females. (A) Lateral view of a 1-month-old female (zpc: eGFP-dnd 3'UTR) shows GFP gonad through the body wall. (B) & (C) Dissected ovaries from 3 month old female (askopos: eGFP-dnd 3'UTR), where the strongest GFP expression is observed in oocytes stage I and II.

We observed a dramatic reduction in PGC count in microinjected embryos compared to mock injected control (FIG. 8C3). Embryos with no detectable PGCs showed no somatic defect. These results support the notion of a well-conserved mechanism of programmed cell death in these distant teleost clades. To further substantiate this claim, we produced zebrafish bax:dnd mRNA from linearized plasmid (Litmus 28i-T7:bax:dnd 3'UTR). Fertilized one-cell stage salmon embryos were split into three groups and microinjected with: (i) zbax:dnd and eGFP:nos1 mRNAs (GFP mRNA is used for germ cell labeling), (ii) eGFP:nos1 mRNA alone and (iii)zbax:dnd mRNA alone. Because the batch of fertilized eggs in this study had a poor survival rate (see table 2) GFP analysis was performed on small sample size. Nevertheless, 3 out of the 9 eGFP:nos1 treated embryos displayed detectable GFP cells while no GFP signal was observed in any of the 6 eGFP:nos1; zbax:dnd treated embryos (Table 2).

TABLE 2

| Injected mRNA | Number of eggs injected | Surviving embryos | % fertilization | GFP positive |
|---|---|---|---|---|
| zBax:dnd + GFP:nos | 103 | 6 | 5.83 | 0 |
| zBax:dnd 127 | 127 | 6 | 4.72 | 0 |
| GFP:nos | 142 | 9 | 6.34 | 3 |
| Control non injected | 108 | 9 | 8.33 | 0 |

What is claimed is:

1. A method of propagating a hemizygous Maternal Sterility Construct (MSC) transgenic male fish comprising:
   (i) obtaining a MSC comprising: (a) a promoter that is specifically active in a developing oocyte during oogenesis; (b) a pro-apoptotic polynucleotide sequence that ablates primordial germ cells (PGCs) after fertilization of the oocyte; and (c) a germ-cell-specific 3' untranslated region (UTR), wherein (a), (b), and (c) are operably linked;
   (ii) introducing the MSC to a fish embryo to generate a male MSC-transgenic founder fish carrying the construct in its germ cell;
   (iii) identifying and breeding the MSC-transgenic male founder fish from step (ii) to produce a hemizygous MSC-transgenic male fish carrying the construct in its germ cell; and
   (iv) breeding the hemizygous MSC-transgenic male fish with a female fish of the same species lacking the MSC to produce a lineage ending female progeny that express MSC and is fertile; and a hemizygous MSC-transgenic male progeny that expresses the MSC;
   wherein the method is carried out in a fish species with germ cells that are specified by maternally inherited determinants according to a pre-formation process.

2. The method of claim 1, further comprising breeding the hemizygous MSC-transgenic male progeny from step (iv) with a female fish of the same species lacking the MSC to propagate a line of hemizygous MSC-transgenic male fish.

3. The method of claim 1, further comprising breeding the lineage-ending female progeny with a male fish of the same species to generate a sterile progeny.

* * * * *

UNITED STATES PATENT AND TRADEMARK OFFICE
CERTIFICATE OF CORRECTION

PATENT NO. : 10,194,644 B2
APPLICATION NO. : 14/928463
DATED : February 5, 2019
INVENTOR(S) : Xavier Lauth and John T. Buchanan Page 1 of 1

It is certified that error appears in the above-identified patent and that said Letters Patent is hereby corrected as shown below:

On the Title Page

Replace item (63) to read:
--Continuation of application No. 13/511,317, filed Aug. 8, 2012, (now Pat. No. 9,198,404) which is a 371 of application No. PCT/US2010/057863, filed Nov. 23, 2010--

Signed and Sealed this
Eighteenth Day of June, 2019

Andrei Iancu
*Director of the United States Patent and Trademark Office*